(12) United States Patent
Ahluwalia et al.

(10) Patent No.: US 10,881,423 B2
(45) Date of Patent: *Jan. 5, 2021

(54) SURGICAL MORCELLATOR

(71) Applicants: Prabhat Kumar Ahluwalia, Little Falls, NY (US); Puja Ahluwalia, Little Falls, NY (US)

(72) Inventors: Prabhat Kumar Ahluwalia, Little Falls, NY (US); Puja Ahluwalia, Little Falls, NY (US)

( * ) Notice: Subject to any disclaimer, the term of this patent is extended or adjusted under 35 U.S.C. 154(b) by 260 days.

This patent is subject to a terminal disclaimer.

(21) Appl. No.: 15/879,546

(22) Filed: Jan. 25, 2018

(65) Prior Publication Data

US 2018/0161054 A1   Jun. 14, 2018

Related U.S. Application Data

(63) Continuation of application No. 15/333,744, filed on Oct. 25, 2016, now Pat. No. 9,913,654, which is a continuation of application No. PCT/US2015/028081, filed on Apr. 28, 2015.

(60) Provisional application No. 61/985,273, filed on Apr. 28, 2014.

(51) Int. Cl.
*A61B 17/32* (2006.01)
*A61B 90/00* (2016.01)
*A61B 17/00* (2006.01)

(52) U.S. Cl.
CPC .......... *A61B 17/32002* (2013.01); *A61B 2017/00398* (2013.01); *A61B 2017/00818* (2013.01); *A61B 2017/320024* (2013.01); *A61B 2017/320064* (2013.01); *A61B 2090/08021* (2016.02); *A61B 2217/005* (2013.01)

(58) Field of Classification Search
CPC ... A61B 17/32; A61B 17/32002; A61B 17/24; A61B 17/320783; A61B 2017/00398; A61B 2017/00818; A61B 2017/320024; A61B 17/320016; A61B 17/29
See application file for complete search history.

(56) References Cited

U.S. PATENT DOCUMENTS

| | | | |
|---|---|---|---|
| 4,368,734 A * | 1/1983 | Banko | A61F 9/00763 606/107 |
| 5,346,497 A | 9/1994 | Simon et al. | |
| 5,561,397 A | 10/1996 | Kumar et al. | |
| 5,685,840 A | 11/1997 | Schechter et al. | |
| 6,045,566 A | 4/2000 | Pagedas | |
| 6,419,684 B1 | 7/2002 | Heisler et al. | |
| 8,308,746 B2 | 11/2012 | Pravong et al. | |
| 8,647,257 B2 | 2/2014 | Jansen et al. | |
| 9,913,654 B2 * | 3/2018 | Ahluwalia | A61B 17/32002 |
| 2004/0034380 A1 | 2/2004 | Woolfson et al. | |
| 2008/0039880 A1 | 2/2008 | Nohilly et al. | |
| 2008/0039883 A1 | 2/2008 | Nohilly | |
| 2015/0018837 A1 | 1/2015 | Sartor et al. | |

* cited by examiner

*Primary Examiner* — Vi X Nguyen
(74) *Attorney, Agent, or Firm* — Pierson Intellectual Property LLC

(57) ABSTRACT

Embodiments described a shield for a surgical morcellator. Specifically, embodiments disclose a denticulate shield for the distal tip of a surgical morcellator with notches, wherein the notches are configured to catch loose morcellated tissue and prevent the loose morcellated tissue from being falling or remaining into the patient.

9 Claims, 30 Drawing Sheets

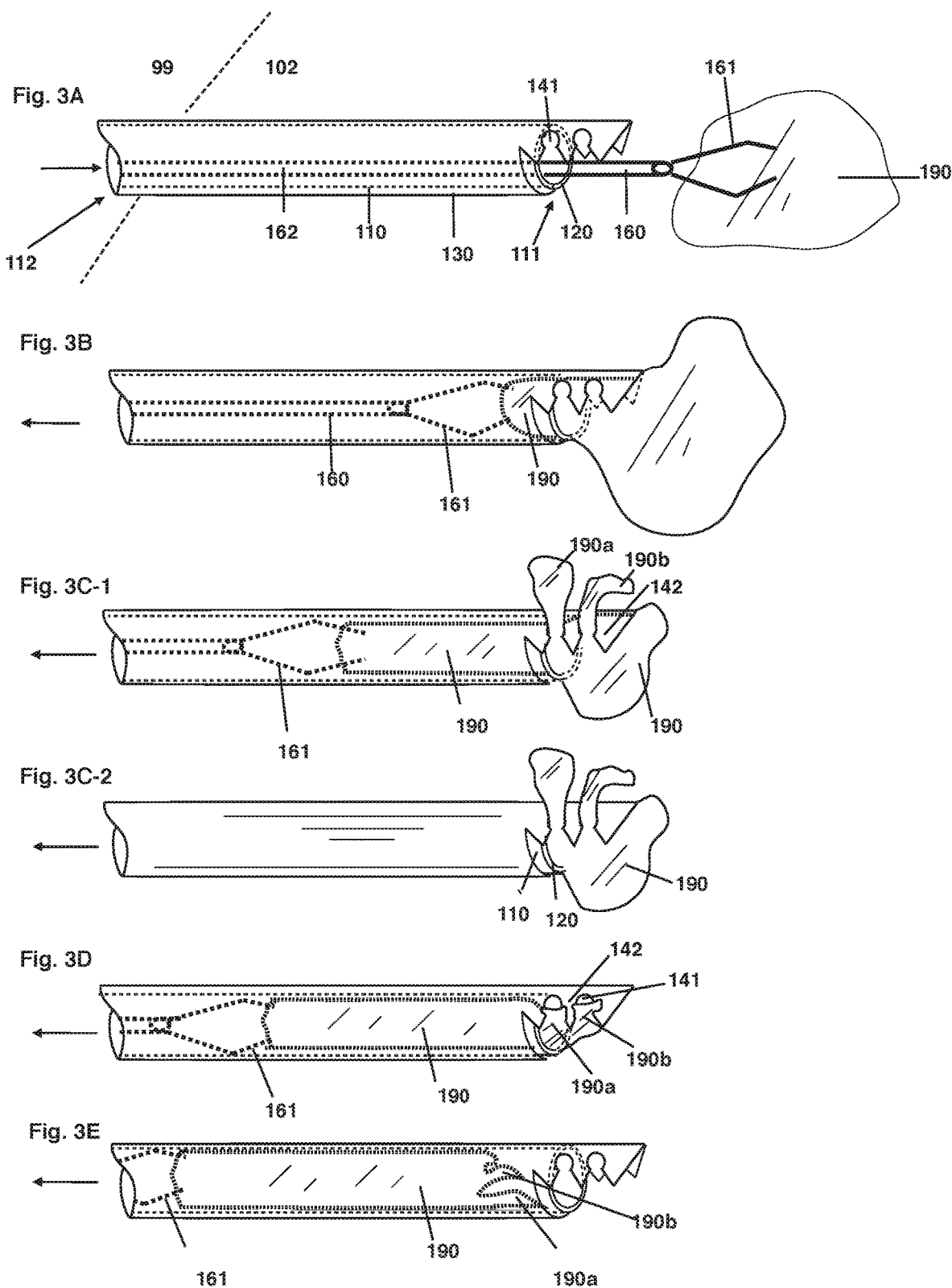

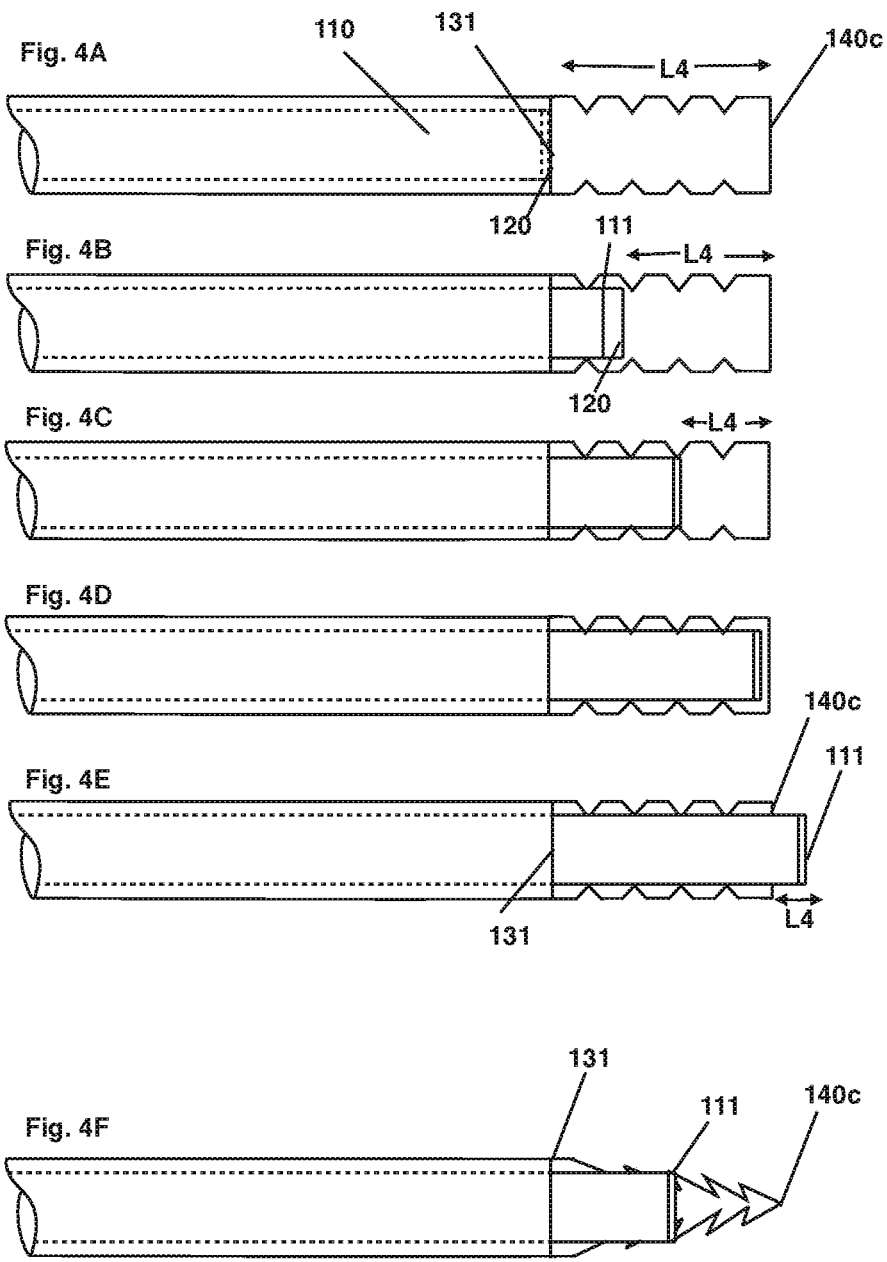

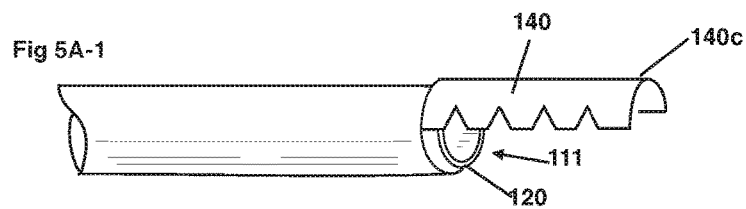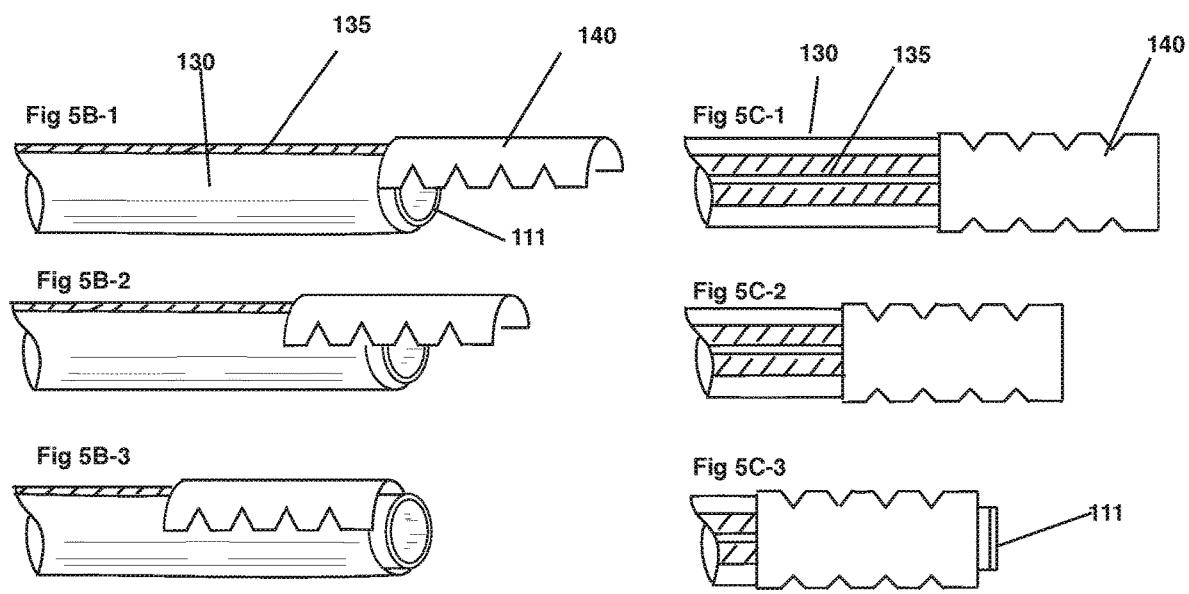

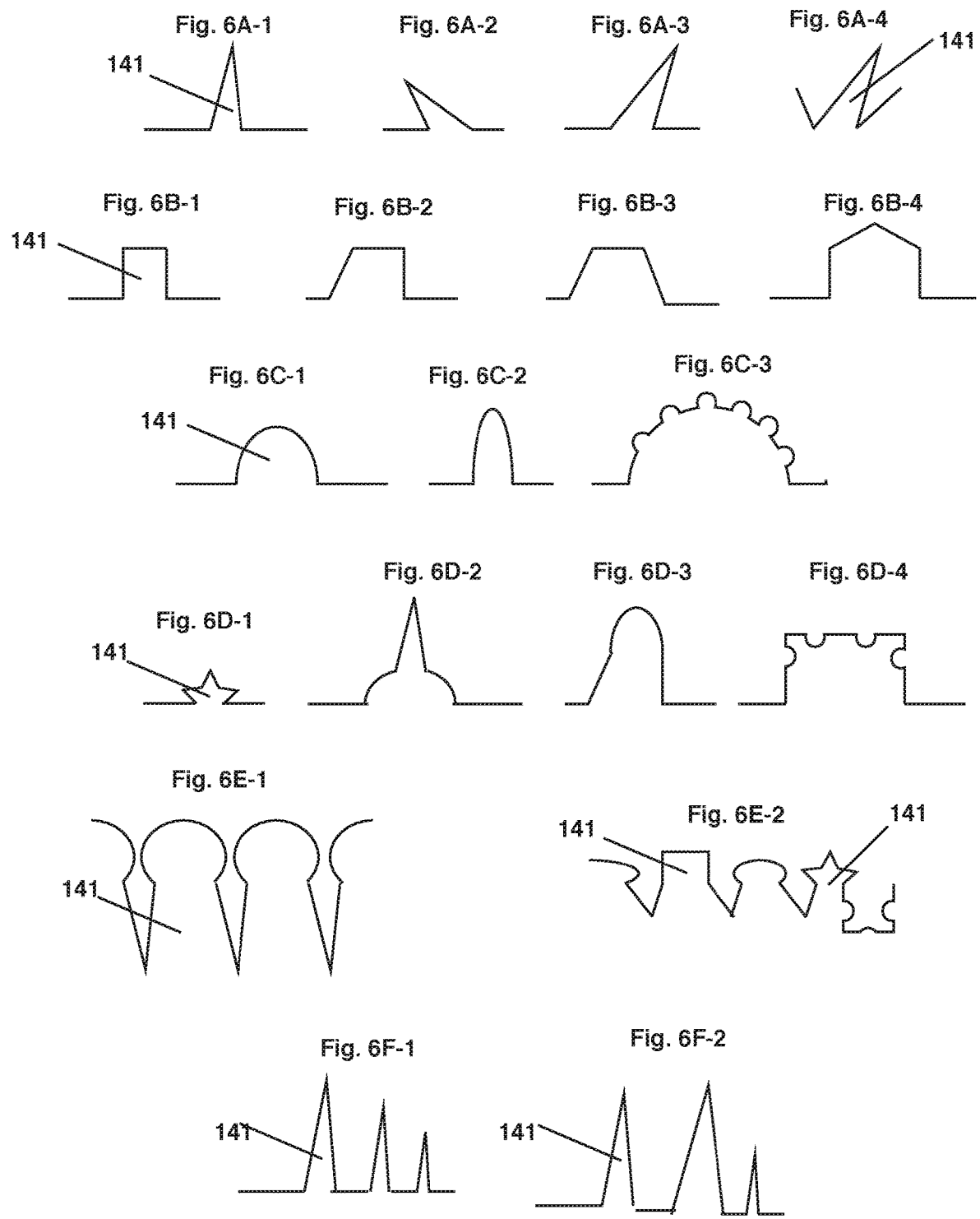

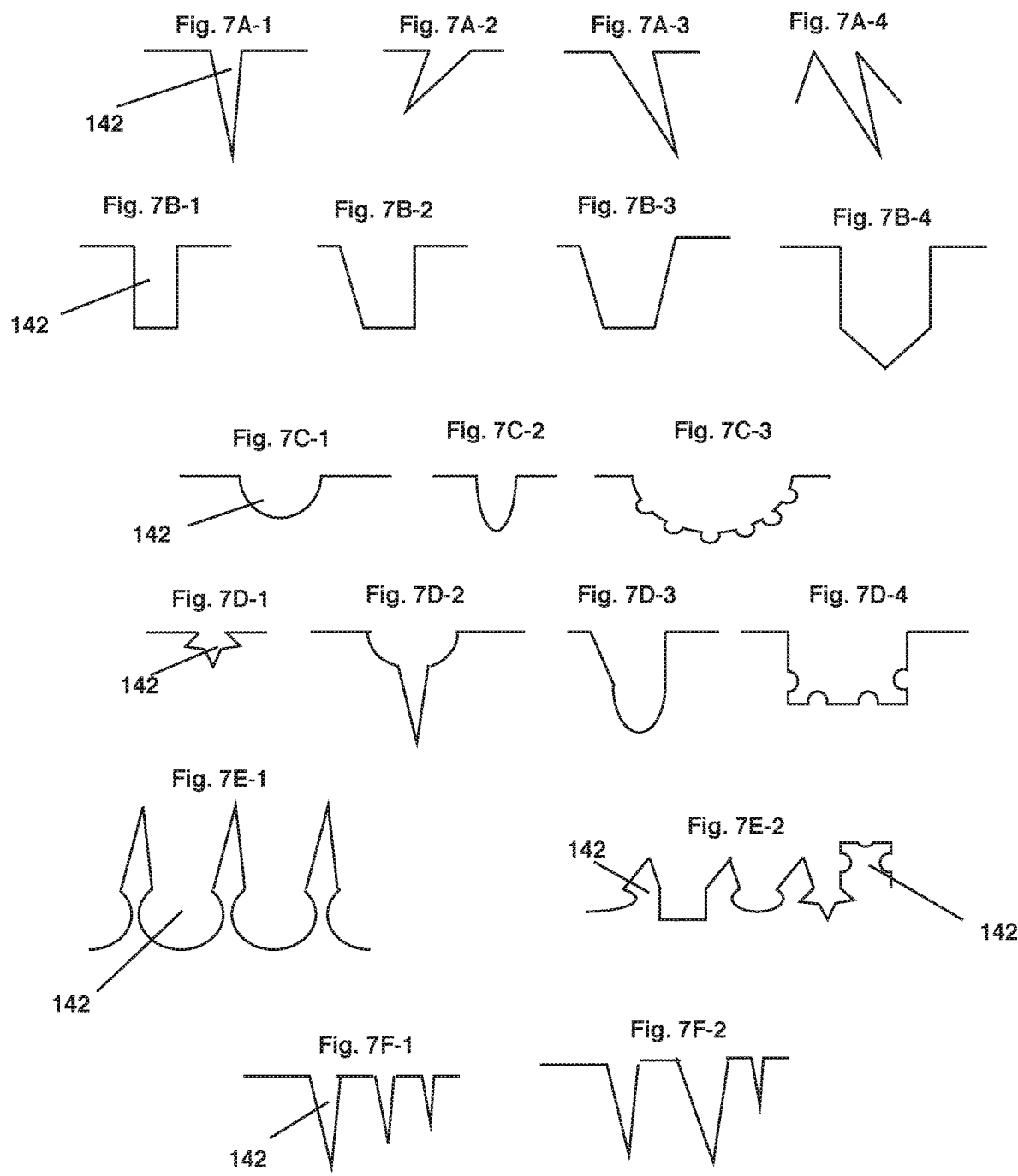

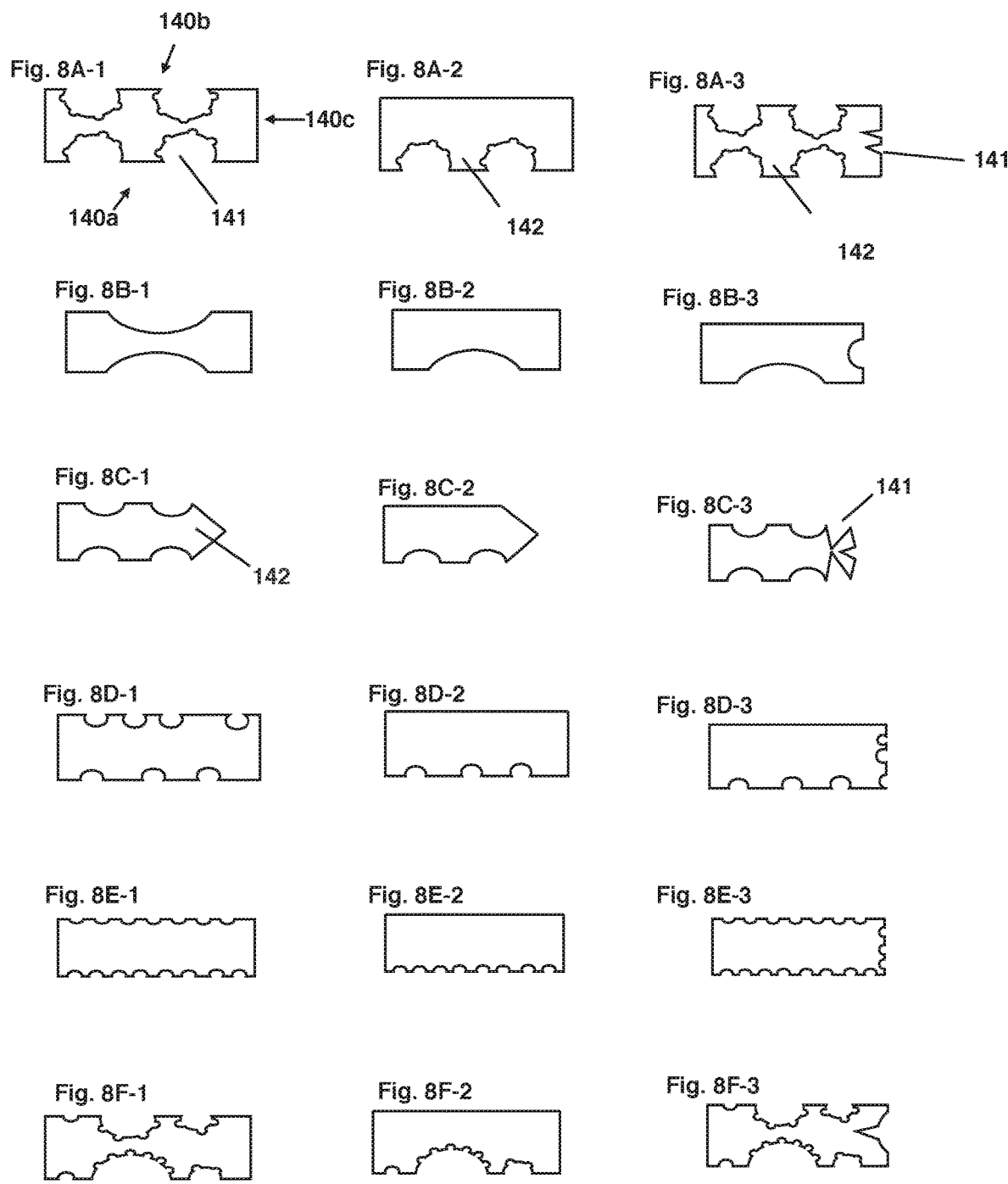

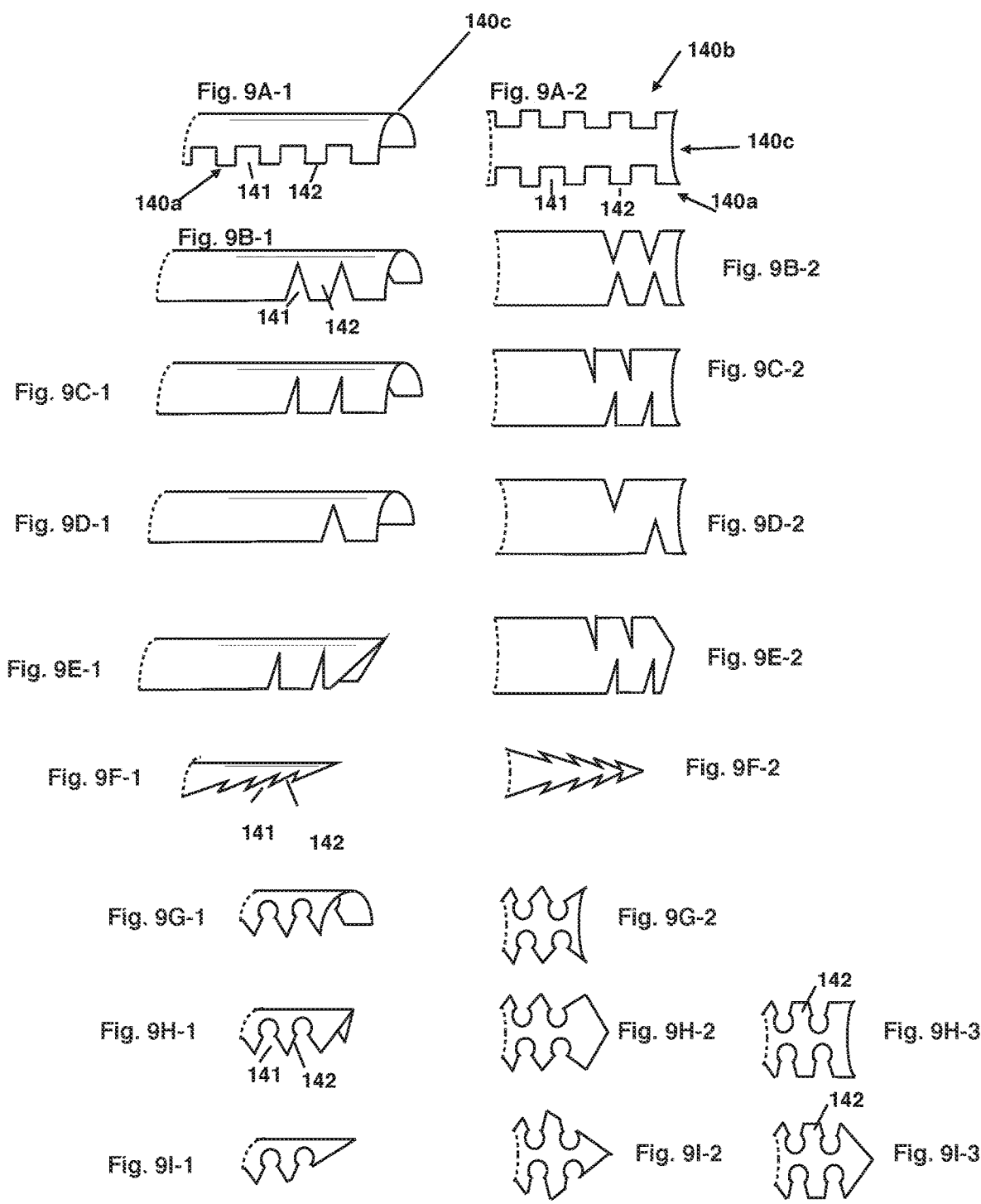

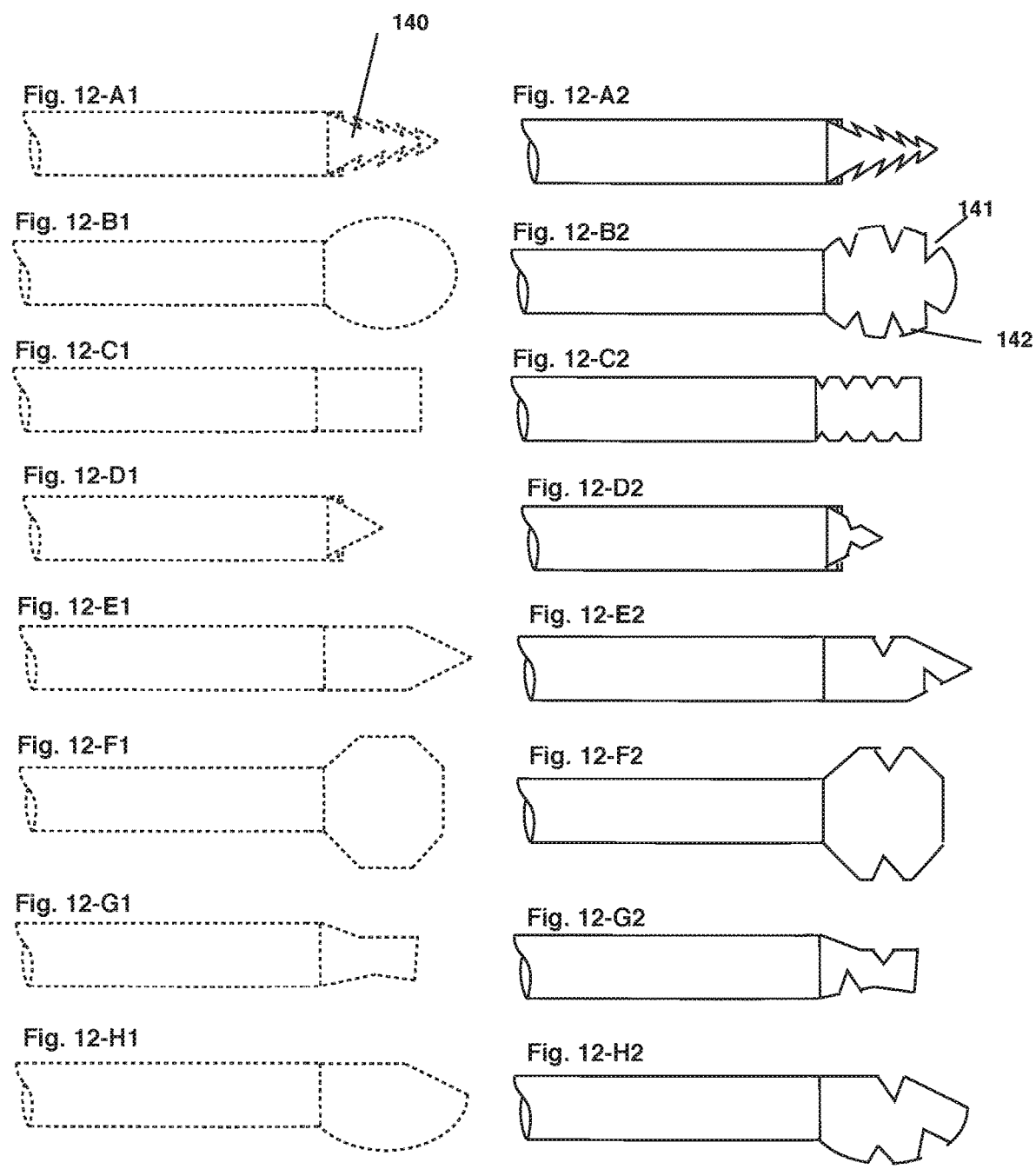

Fig. 19A
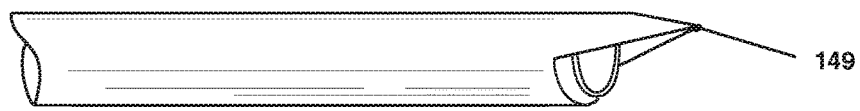
Fig. 19B
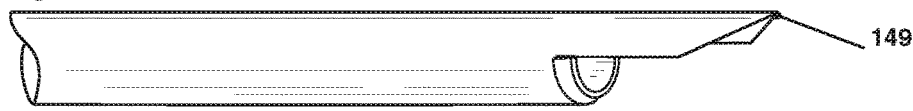
Fig. 19C
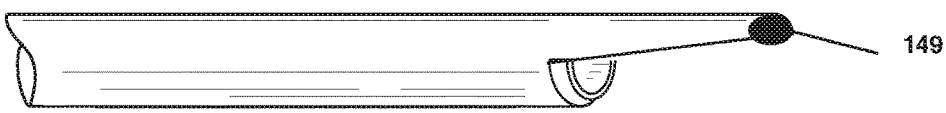
Fig. 19D
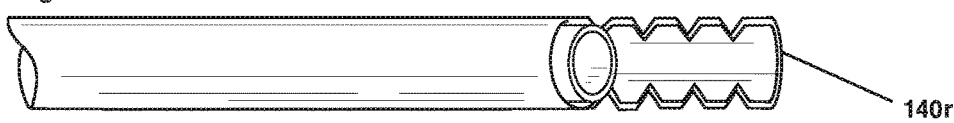
Fig. 19E
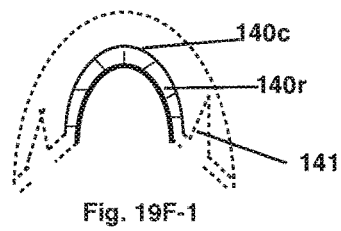
Fig. 19F-1
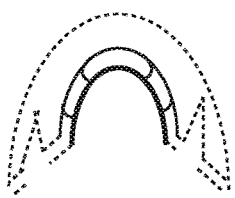
Fig. 19F-2
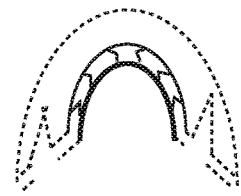
Fig. 19F-3
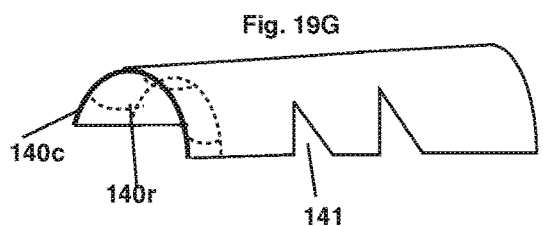
Fig. 19G
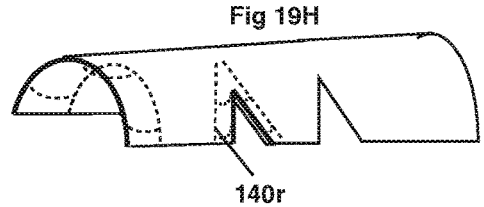
Fig 19H

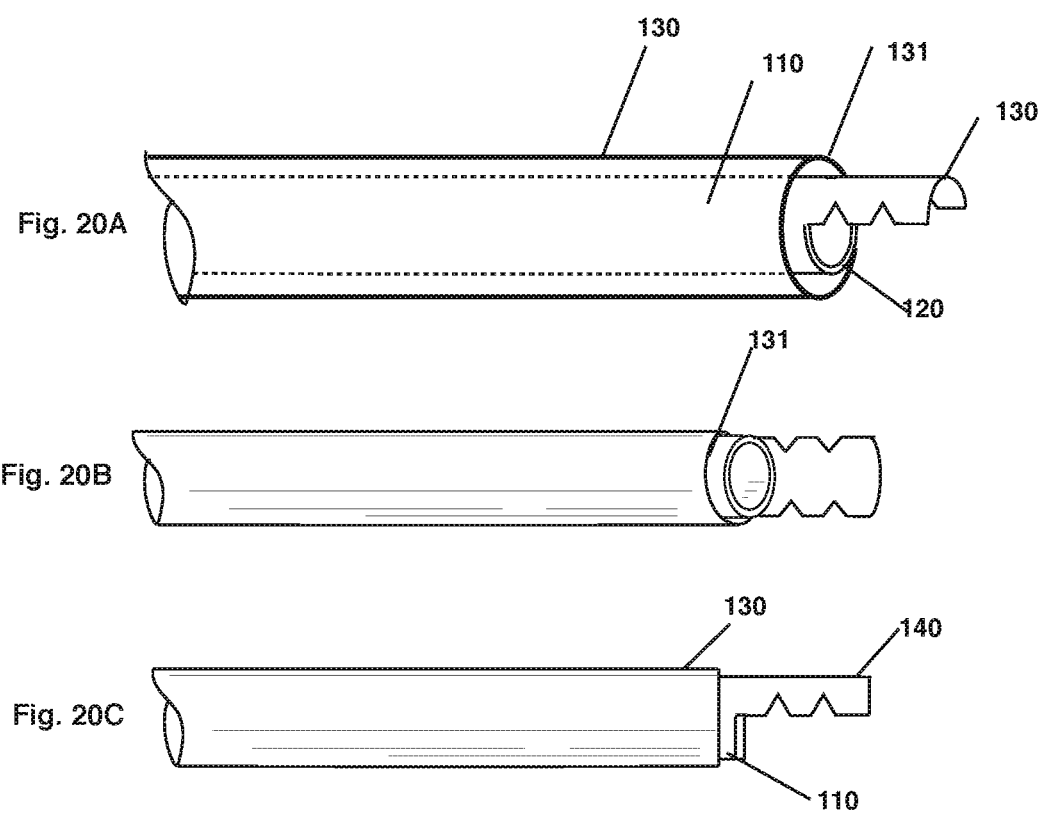

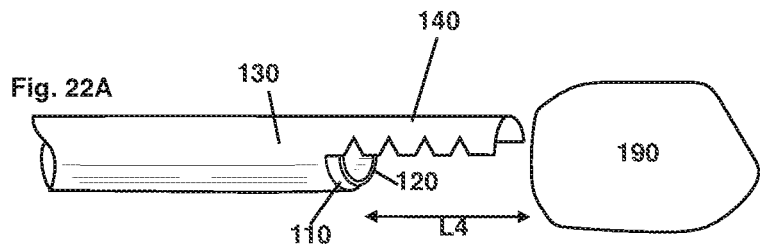
Fig. 22A
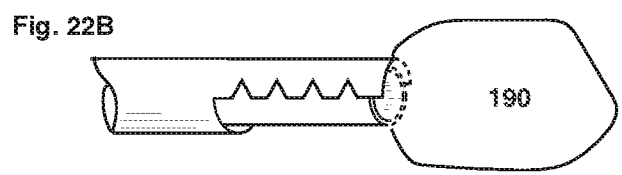 
Fig. 22B
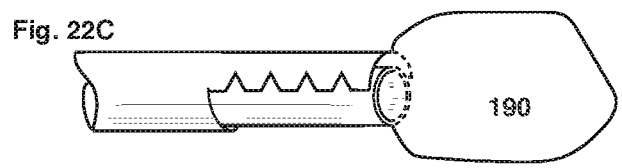 
Fig. 22C
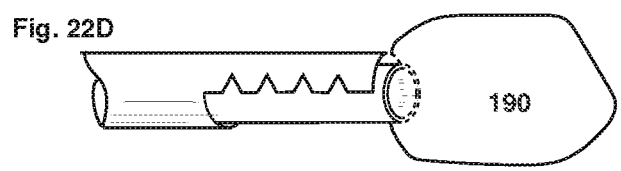 
Fig. 22D
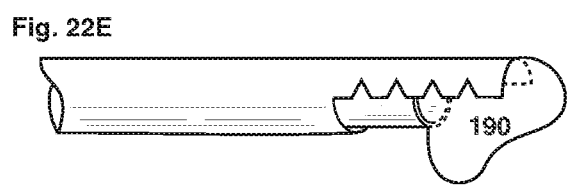 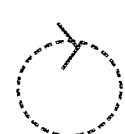
Fig. 22E
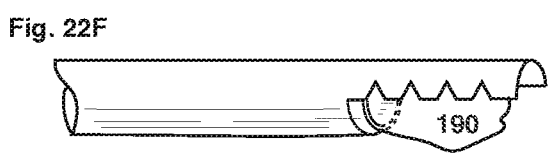 
Fig. 22F

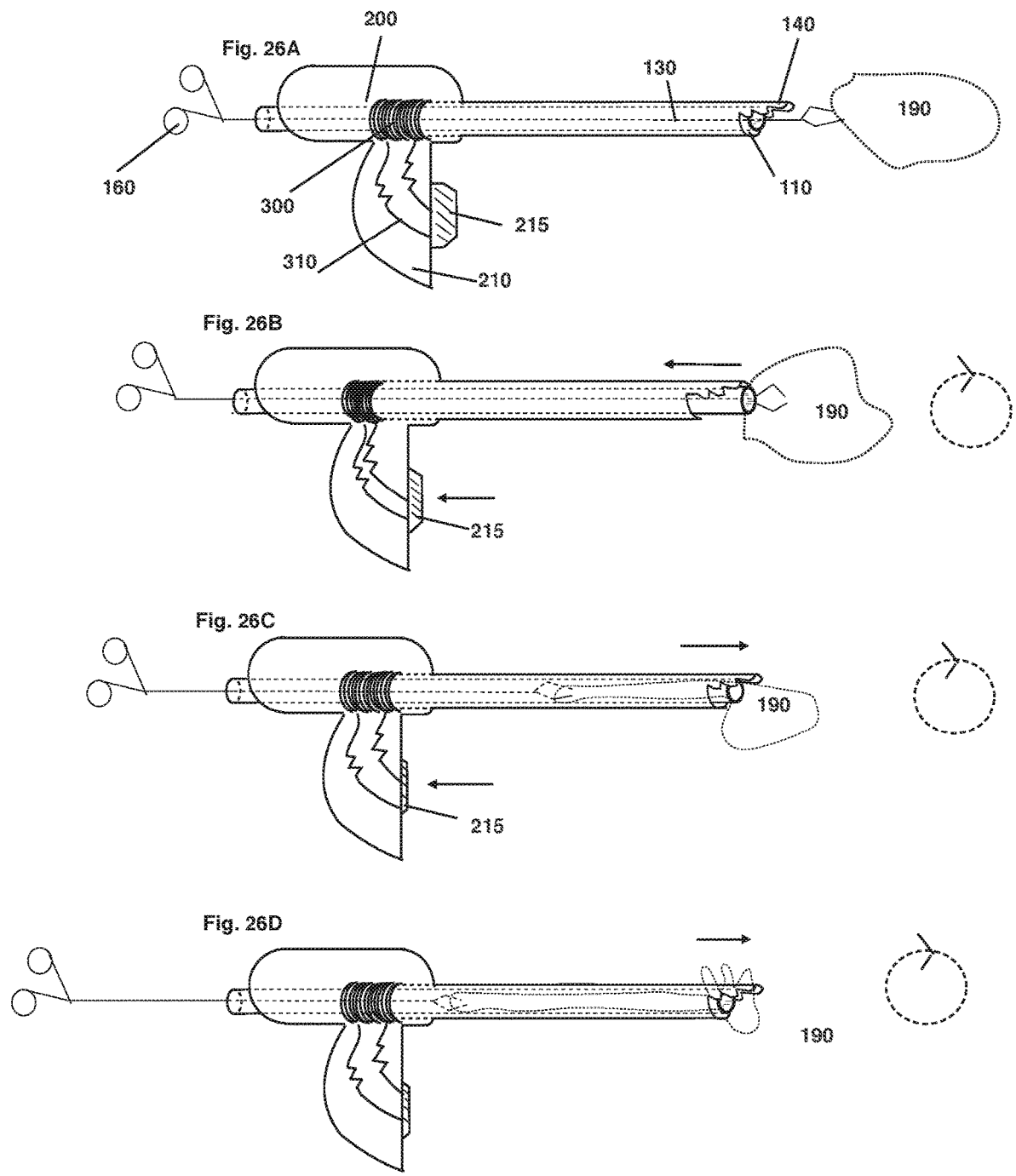

SURGICAL MORCELLATOR

CROSS-REFERENCE TO RELATED APPLICATIONS

This application is a continuation under 35 U.S.C. § 120 to PCT/US2015/28081 filed on Apr. 28, 2015, which claims a benefit of priority under 35 U.S.C. § 119 to U.S. Provisional Patent Application No. 61/985,273 filed Apr. 28, 2014, which are hereby fully incorporated herein by reference in its entirety.

BACKGROUND INFORMATION

Field of the Disclosure

The structures and methods of the present invention will significantly facilitate the severing and removal of tissues from internal surgical sites during both minimally invasive and traditional open surgical procedures. These methods and structures are particularly well adapted, however, for laparoscopic procedures requiring removal of significant masses of tissues, such as for removal of a large fibroid or cancerous tissue, using a morcellation device.

Background

Minimally invasive surgical procedures, such as laparoscopic and robotic surgery procedures, often require the removal large masses of tissue. For example a surgeon may need to remove a uterine fibroid or a large cancerous mass from the peritoneal cavity without making a large incision into the patient. Morcellators assist surgeons in severing and removing large tissue masses from the patient in minimally invasive surgery.

Conventionally, a morcellator includes a rotating cylindrical inner tube having a sharp distal cutting edge, which rotates within a stationary outer tube. The morcellator is inserted into the patient through a cannula or trocar, or directly through an incision. Access and optical visualization of such tissue removal procedures is generally facilitated by pneumo-peritoneum (gas insufflation), and by positioning of an endoscope, laparoscope, or the like, within the distended body cavity.

A surgeon inserts the grasping instrument (i.e., tenaculum) through the cylindrical tube, grasps the tissue for morcellation, and pulls the tissue through the inside lumen of the tube. When the grasper or tenaculum pulls the tissue through the tube, the tissue is positioned adjacent to the cutting edge or circumference of the tube, which cuts, severs, or morcellates the tissue. By repeating the grasping and severing procedure, the surgeon can remove the large tissue mass incrementally.

FIGS. 1A-1C depict a conventional hand-held morcellator 100 intended to divide and remove large masses of tissue during surgery. FIG. 1A shows a morcellator 100 inserted into a peritoneal cavity 102 of a patient 103. Tissue mass 190 is removed from cavity 102 by grasping and pulling tissue mass 190 through morcellator's inner tube 110 using a grasper or tenaculum (hereinafter "tenaculum 160"). The distal end of inner tube 110 contains a cutting edge, which is operated by a motor. By positioning tissue mass 190 in contract with a cutting edge and pulling morcellated tissue mass 190 through inner tube 110, tissue mass 190 is cut, retrieved and removed from the patient.

FIGS. 1B-1C show another prior art morcellator 100. FIG. 1B shows an outer tube 130 having a distal end 131 in contact with tissue mass 190. FIG. 1C shows the outer tube 130 encasing an inner tube 110, wherein a surgeon inserts a grasper or tenaculum 160 to pull and cut the tissue mass 190.

In this prior art device, a morcellator includes a cylindrical inner lumen, driving shaft or tube (hereinafter "inner tube 110"). Inner tube 110 has a sharp distal cutting edge, which rotates within a stationary outer tube 130. A motor conventionally positioned in a proximal portion of the morcellator, for example in handle 200, powers rotation of the cutting edge.

After the organ or tissue mass 190 has been severed from the patient, a morcellator is inserted into a patient through a cannula or trocar, or directly through an incision. A surgeon inserts a grasping instrument (i.e., tenaculum 160) through inner tube 110, grasps tissue mass 190, for morcellation, and pulls the tissue mass 190 through the inside lumen of inner tube 110. When tissue mass 190 is positioned adjacent to cutting edge 120 or circumference of inner tube 110, cutting edge 120 cuts, severs, or morcellates the tissue. By repeating the severing and grasping procedure, a surgeon removes tissue mass 190 incrementally.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIGS. 3A, 3B, 3C-1, 3C-2, 3D, 3E depict operation of an embodiment of a morcellator with a tissue mass.

FIGS. 4A, 4B, 4C, 4D, 4E, 4F depict embodiments of a morcellator distal portion with alternative positions of an inner tube, cutting edge, outer tube and shield.

FIGS. 5A-1, 5A-2, 5A-3 depict embodiments of a morcellator distal portion with alternative positions of a shield in relation to the inner tube and outer.

FIGS. 5B-1, 5B-2, 5B-3, 5C-1, 5C-2, 5C-3 depict embodiments of a morcellator distal portion, showing a retractable shield configured for sliding on a track.

FIGS. 6A-1, 6A-2, 6A-3, 6A-4, 6B-1, 6B-2, 6B-3, 6B-4, 6C-1, 6C-2, 6C-3, 6D-1, 6D-2, 6D-3, 6D-4, 6E-1, 6E-2, 6F-1, 6F-2 depict possible embodiments of a notch configured to capture loose tissue fragments on a shield of a morcellator.

FIGS. 7A-1, 7A-2, 7A-3, 7A-4, 7B-1, 7B-2, 7B-3, 7B-4, 7C-1, 7C-2, 7C-3, 7D-1, 7D-2, 7D-3, 7D-4, 7E-1, 7E-2, 7F-1, 7F-2 depict possible embodiments of an arm configured to capture loose tissue fragments on a shield of a morcellator.

FIGS. 8A-1, 8A-2, 8A-3, 8B-1, 8B-2, 8B-3, 8C-1, 8C-2, 8C-3, 8D-1, 8D-2, 8D-3, 8E-1, 8E-2, 8E-3, 8F-1, 8F-2, 8F-3 illustrate plan views of embodiments of a morcellator shield, and further illustrate possible configurations of arms and notches along the shield's perimeter of shield.

FIGS. 9A-1, 9A-2, 9B-1, 9B-2, 9C-1, 9C-2, 9D-1, 9D-2, 9E-1, 9E-2, 9F-1, 9F-2, 9G-1, 9G-2, 9H-1, 9H-2, 9H-3, 9I-1, 9I-2, 9I-3 depict embodiments of a shield configured for capturing loose tissue on a morcellator.

FIGS. 10A-1, 10A-2, 10-B-1, 10B-2, 10C-1, 10C-2, 10D-1, 10D-2 depict embodiments of a shield coupled to a morcellator's distal end.

FIGS. 12-A1, 12-A2, 12-B1, 12-B2, 12-C1, 12-C2, 12-D1, 12-D2, 12-E1, 12-E2, 12-F1, 12-F2, 12-G1, 12-G2, 12-H1, 12-H2 depict plan views of various shield shapes for a morcellator.

FIGS. 14-A1, 14-A2, 14-B1, 14-B2, 14-C1, 14-C2, 14-D1, 14-D2, 14-E1, 14-E2 depict curved shield shapes for a morcellator.

FIGS. 15-A1, 15-A2, 15-B1, 15-B2, 15-C1, 15-C2, 15-D1, 15-D2, 15-E1, 15-E2, 15-F1, 15-F2, 15-G1, 15-G2, 15-H1, 15-H2 depict angled shield shapes for a morcellator.

FIGS. 16A-0, 16A-1, 16A-2, 16A-3, 16B-0, 16B-1, 16B-2, 16B-3, 16B-4 depict embodiments of shield, showing variation of circumference and shape.

FIGS. 18A-1, 18A-2, 18B-1, 18B-2, 18C-1, 18C-2 illustrate side and bottom views embodiments of a morcellator containing notches and arms on one sidewall of a shield.

FIGS. 19A-19B-19C show embodiments of a knot, mass, or knob configured for a distal portion of a shield.

FIGS. 19D, 19E, 19F-1, 19F-2, 19F-3, 19G, 19H illustrate a rim component for a shield and morcellator.

FIGS. 20A, 20B, 20C illustrate a perspective, bottom and side views respectively of another embodiment wherein a shield is coupled to an inner tube of a morcellator.

FIGS. 22A, 22B, 22C, 22D, 22E, 22F illustrate operation of an embodiment of a morcellator with a tissue mass wherein a shield is coupled or integrated with a retractable outer tube.

FIGS. 26A, 26B, 26C, 26D illustrate another embodiment wherein the retraction of outer tube and/or morcellation is accomplished with a button actuated spring mechanism in the morcellator handle.

Figure 1A:
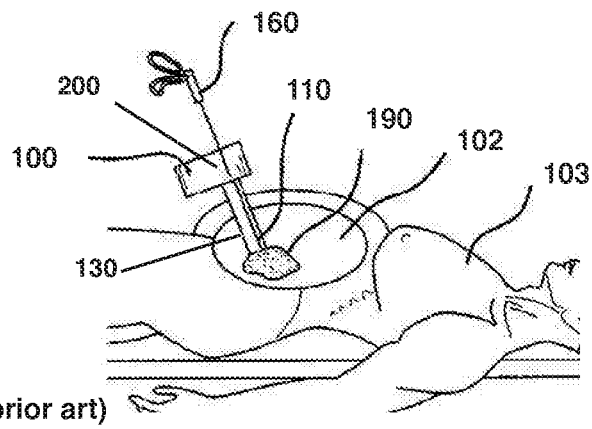
FIG. 1A depicts a conventional morcellator for minimally invasive surgery.
Figure 1B:
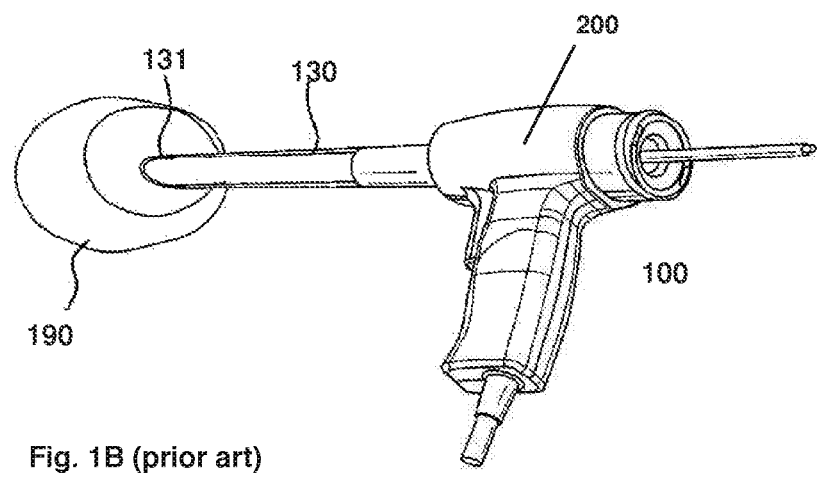
FIGS. 1B-1C depict perspective views of a conventional morcellator for minimally invasive surgery.
Figure 1C:
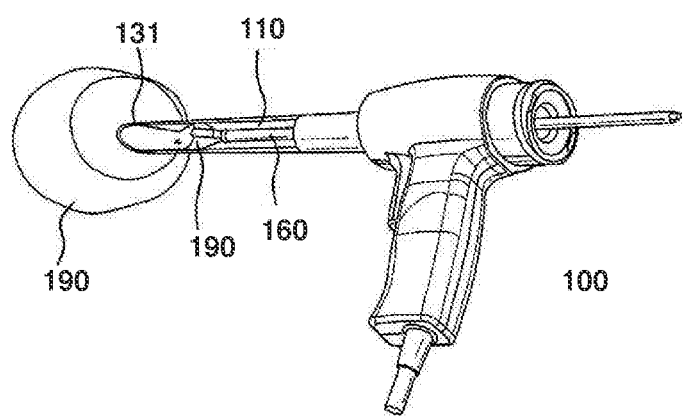

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, numerous specific details are set forth in order to provide a thorough understanding of the present embodiments. It will be apparent to one having ordinary skill in the art, that the specific detail need not be employed to practice the present embodiments. In other instances, well-known materials or methods have not been described in detail in order to avoid obscuring the present embodiments.

Although morcellators are functional for reducing tissue mass, the inventors observe conventional morcellation technology presents several challenges and risks. First, when the tissue is pulled into the cutting edge, smaller pieces of the tissue, sometimes cancerous, are left rotating around the cutting edge and may displaced or disseminated into the patient's peritoneal cavity and onto neighboring organs and critical structures. Without being constrained herein to theory, this may be the result of a disproportional pull force on the tissue and increased friction between the tissue and rotating cutting edge. Accordingly, the need exists for more efficient and effective methods and systems to trap morcellated pieces of tissue and prevent them from being disseminated into the peritoneal cavity or patient's body.

Second, there is a lag in time between the surgeon's observation that morcellation is no longer required and termination of morcellation procedure, so called the response time. This is because the cutting edge rotates for some time after the surgeon intends to stop morcellation. Tissue injury results from this lag in response time.

In addition, surgeons achieve morcellation by pulling tissue with a tenaculum into the rotating cutting edge. Surgeons also have tendency to push the morcellator into the tissue. Injury to nearby tissue and organs occurs when pull and push forces are coupled excessively in conjunction with lags in response time.

FIGS. 2A-2G show one embodiment of the present invention including a morcellator's distal portion 101 (hereinafter "morcellator's distal end 101"). Morcellator's distal end 101 may be configured for a distal portion of a conventional hand-held morcellator device or for a distal portion of a conventional robotic arm morcellator.

Figure 2A:
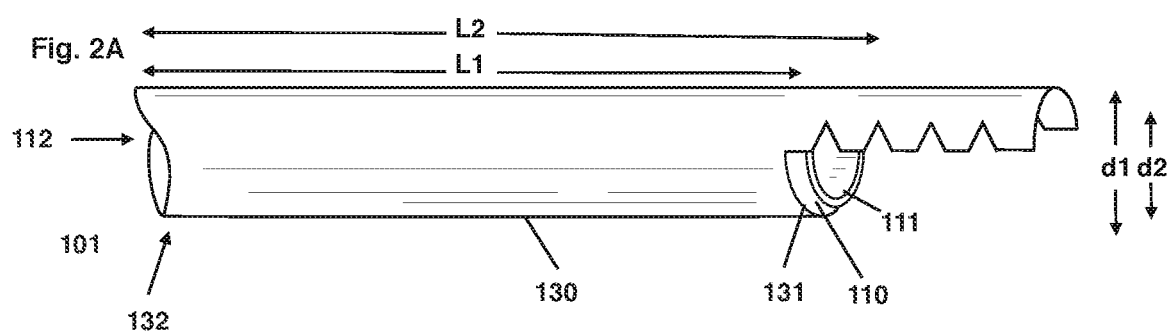
FIGS. 2A, 2B, 2C, 2D, 2E, 2F, 2G depict perspective views of an embodiment of a morcellator's distal portion.
Figure 2B:
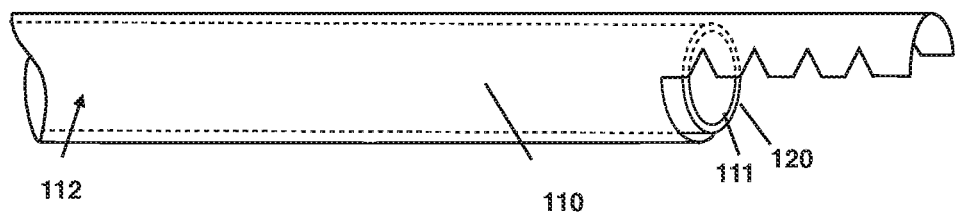
Figure 2C:
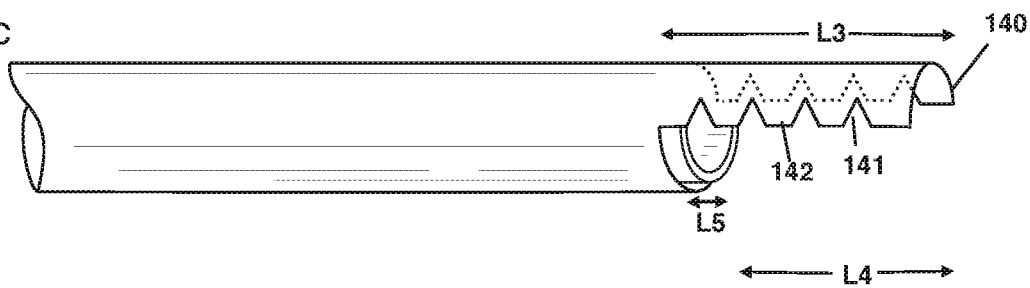
Figure 2D:
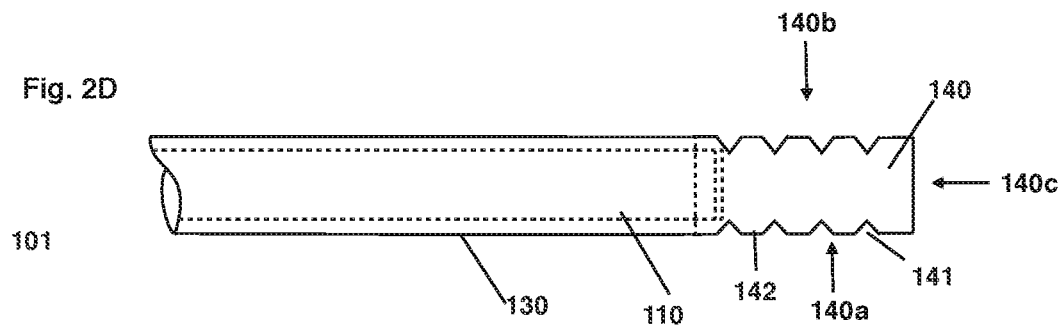
Figure 2E:
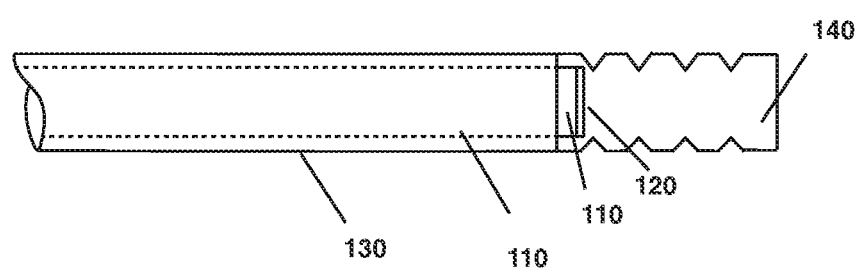
Figure 2F:
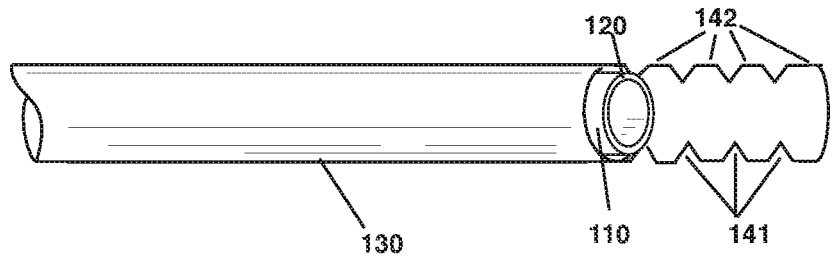
Figure 2G:
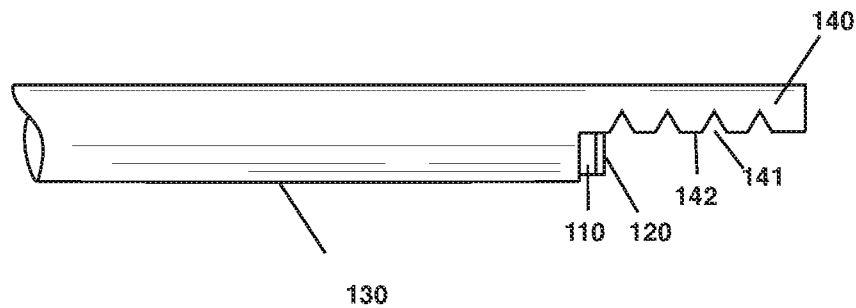

Morcellator's distal end 101 comprises an outer tube 130 configured for coupling, integration or attachment to a denticulate shield 140, and an inner tube 110 configured for coupling, integration or attachment to a cutting edge 120. FIGS. 2A-C illustrate a perspective view of an embodiment. FIG. 2D is a plan view. FIG. 2E is a bottom view. FIG. 2F is a perspective view. FIG. 2G is a side view.

As shown in FIG. 2A, morcellator's distal end 101 includes an outer tube 130, having a first diameter d1, a first length L1, a first distal end 131, and a first proximal end 132. First distal end 131 is open, and outer tube 130 includes a tubular section or a hollow cylinder between first distal end 131 and first proximal end 132. Outer tube 130 may have a circular cross-section, as shown, or any polygonal, trapezoidal, circular, oval or mixed shape cross-section. Outer tube 130 receives an inner tube 110.

Morcellator's distal end 101 also includes inner tube 110, having a second diameter d2, a second length L2, a second distal end 111 (hereinafter "inner tube's distal end 111"), and a second proximal end 112 (hereinafter "inner tube's proximal end 112"), wherein inner tube's second diameter d2 is less than first diameter d1 of outer tube 130. Inner tube's distal end 111 is open. Inner tube 110 includes a tubular section or a hollow cylinder between inner tube's distal end 111 and inner tube's proximal end 112 to retrieve tissue mass 190 via a grasper or tenaculum.

Inner tube 110 has a circular cross-section, as shown, but in other embodiments it may have any polygonal, trapezoidal, circular, oval or mixed shape cross-section. Additionally, inner tube 130 is hollow between distal end 111 and first proximal end 112, but in other embodiments inner tube may be partially hollow.

In embodiments, inner tube 110 may be configured to be fixed in place along a longitudinal axis forming an axis of rotation, such that inner tube 110 may not be axially translated. Inner tube 110 may also include a spacer configured as a one or more tab(s), ball(s), mass(es) or protrusion(s) to maintain a distance between inner tube 110 and outer tube 130 and hold inner tube 110 fixed in place.

In some embodiments, as shown in FIGS. 2A-F, at least a portion of inner tube 110 is configured to be partially or completely encased, surrounded, or sheathed within outer tube 130. In some embodiments, as shown in FIGS. 2A-F, inner tube's distal end 111 extends distally beyond outer tube's distal end 131. Hence, inner tube's length L2 may be greater than outer tube's length L1.

As shown in FIG. 2B, inner tube's distal end 111 is configured to couple, receive or integrate a cutting edge 120. Cutting edge 120 has an axis of rotation and may be configured to rotate in a clockwise or counterclockwise direction to cut tissue mass 190. A rotating drum, wheel or motor positioned in a proximal portion of the morcellator, for example in handle 200, may power the rotation of the cutting edge. Cutting edge 120 is configured to interface with tissue mass 190. Responsive to cutting edge 120 being rotated, cutting edge 120 slices, cuts, or morcellates tissue mass 190 into smaller pieces of tissue.

In other embodiments, cutting edge 120 is located within an annular space between inner tube 110 and outer tube 130, is coupled to outer tube 130, or is coupled to any additional tubes coupled to morcellator 100.

Cutting edge 120 may be configured to rotate at a variable rate based on the size of tissue mass 190. For example, if tissue mass 190 is smaller in size, then the rotational speed of cutting edge 120 may be decreased, and if tissue mass 190 is larger in size, then the rotational speed of cutting edge 120 may be increased. The rotational speed of cutting edge 120 may be controlled via a motor, gears, gear ratios and associated settings, axles, resistance, or other mechanical technology. The rotational speed may also be electrically controlled via software, hardware or electro-mechanical assemblies. A rotating drum, wheel or motor positioned in a proximal portion of the morcellator or in the handle 200 may power rotation of the cutting edge, and one or more levers or buttons positioned on the surface of the handle may allow a surgeon to control the speed of morcellation.

As shown in FIGS. 2A-2G, morcellator 100 also includes a hood, tip, or shield (hereinafter "shield 140") configured for coupling, integration or attachment to outer tube's distal end 131, wherein shield 140 is denticulate. Shield 140 extends distally from outer tube's distal end 131 a third length L3. Shield 140 also extends distally from inner tube's distal end 111 a fourth length L4. The distance between the outer tube's distal end 131 and inner tube's distal end 111 is L5.

FIGS. 2A-F illustrates an embodiment where length L4 is less than length L3. As shown, shield 140 may project distally from outer tube 130 in a direction that is planar or linear with a top surface of outer tube 130. However, in other embodiments, shield 140 may project at an angle or may have an adjustable angle with respect to inner tube 110 or outer tube 130.

Shield 140 is denticulate and includes one or more grooves, arms, fingers, teeth protrusions, etc. (referred to hereinafter collectively and individually as "arm(s) 142") separated by one or more gullies, gaps, notches, concavities, indentions, orifices, wedges, or notches 141 (referred to hereinafter collectively and individually as "notch(es) 141").

FIGS. 2A-2F show an embodiment wherein a plurality of arms 142 are separated by plurality of notches 141 to form a denticulate finger, comb, spider, or rake structure on shield 140 configured catch or capture loose tissue morcellated by cutting edge 120.

In conventional morcellators, when cutting edge 120 cuts tissue mass 190, morcellated pieces of tissue may rotate along cutting edge 120 at a speed of rotation of cutting edge 120, eventually disseminating into the patient's cavity. However, utilizing denticulate shield 140 with one or more arm(s) 142 and one or more notch(es) 141 catches loose tissue, preventing or limiting dissemination of potentially cancerous loose tissue into the patient.

Accordingly, in embodiments where cutting edge 120 cuts tissue mass 190, pieces of loose tissue may be caught and secured by a denticulate shield, and in particular shield 140's constituent arms 142 and/or notches 141. In addition, arms 142 and/or notches 141 may include an additional cutting surface or edge to facilitate morcellation. Because shield 140 may be positioned in front of cutting edge 120, arms 142 may be configured to cut tissue mass 190 before tissue mass 190 contacts cutting edge 120.

FIG. 2D is a plan view of an embodiment showing a denticulate shield 140 in greater detail, in particular shield 140's first sidewall 140a, second sidewall 140b, and distal edge 140c. Other embodiments may include additional sidewalls to form a polygonal, trapezoidal, curved or mixed shape, as shown in FIGS. 12A-1 to 12H-2.

In FIG. 2D's embodiment, first sidewall 140a is parallel to sidewall 140b. However, in other embodiments, first sidewall 140a may not be parallel or may be angled with respect to sidewall 140b. Similarly, in this embodiment, distal edge 140c is perpendicular to first sidewall 140a and second sidewall 140b, but in other embodiments it may be angled or curved with respect to the sidewalls.

As shown in FIG. 2D's embodiment, both sidewalls 140a and 140b include arms 142 and/or notches 141. Therefore, arms 142 and/or notches 141 on both sides of shield 140 are configured to catch loose morcellated tissue if cutting edge 120 is spinning in a clockwise direction or a counterclockwise direction.

In other embodiments, however, arms 142 and/or notches 141 may be limited to one sidewall or be positioned on one or more portions of a sidewall. In embodiments where arms 142 and/or notches 141 are positioned on only one sidewall (or on a portion of a sidewall or shield 140), the sidewall including arms 142 and/or notches 141 may be positioned opposite to a direction of rotation of cutting edge 120, or may be positioned towards the direction of rotation of cutting edge 120 to facilitate tissue capturing. Additionally, a sidewall opposite the direction of rotation of cutting edge 120 may be different in shape than another sidewall on shield 140. For example, one or both sidewalls or any portions thereof may be uniquely curved, linear or angled with respect to the longitudinal axis of inner tube 110.

As shown in FIG. 2B's embodiment, shield's distal edge 140c is an arc extending around a single longitudinal axis. In other embodiments, distal edge 140c may be curved or rounded without a sharp corner edge so as to be atraumatic to the patient and not puncture tissue. In other embodiments, the arc may not being constrained to a single axis. Also, distal edge 140c may be angled or peaked, or positioned at an even higher or lower plane than shield 140's proximal end. In addition, distal edge 140c may also include one or more arms 142 and/or notches 141 to facilitate tissue capturing at the shield's distal end.

FIG. 2E is a bottom view, FIG. 2F is a bottom perspective view, and FIG. 2G is a side view of an embodiment illustrated in FIGS. 2A-C, further illustrating the relationship of inner tube 110, outer tube 130, and shield 140.

FIGS. 3A-3E illustrate an operation of an embodiment with a tissue mass 190 intended for morcellation. When a medical practitioner is holding morcellator 100, inner tube's distal end 111 is located within a patient, for example within peritoneal cavity 102 as shown, and a proximal end of inner tube 110 is located outside of a patient in area 99.

FIG. 3A illustrates a first mode of operation wherein a surgeon extends a grasper or tenaculum 160 through inner tube 110 from inner tube's proximal end 112 towards inner tube's distal end 111 to secure tissue mass 190 within cavity 102 for morcellation. In this illustration, tissue mass has a diameter greater than outer tube's diameter d1 and benefits from morcellation.

In this embodiment, tenaculum 160 is surgical instrument held by the surgeon or robotic arm that include slender sharp-pointed distal hooks 161 attached to a shaft 162. The shaft may include a handle on tenaculum 160's proximal end which allows the surgeon or arm to open and close hooks 16. Tenaculum 160 is configured to seize and secure tissue mass 190 and/or an organ within a patient. Tenaculum 160 may have a length that is at least as long the length of the shaft of inner tube 110, and tenaculum 160 is configured to move along the longitudinal axis of the shaft.

As shown in FIG. 3A, responsive to a medical practitioner pushing tenaculum 160, tenaculum 160 is positioned distal to inner tube 110 and secures tissue mass 190 via a grasping mechanism, such as closure of prongs 161 around tissue mass 190. Tenaculum 160 may also include one or more spacers around shaft 162 to prevent the shaft from hitting or sidewalls of inner tube 110 or cutting edge 120.

FIG. 3B illustrates a second mode of operation, wherein responsive to a medical practitioner pulling tenaculum 160, tissue mass 190 (secured by hooks 161 is cut or morcellated by cutting edge 120, and pulled through inner tube 110 from inner tube's distal end 111 towards inner tube's proximal end 112. Inner tube 110 may be configured to transport tissue mass 190 from a location within a patient (e.g., cavity 102) to an area 99 remote or outside the patent patient.

When cutting edge 120 cuts tissue mass 190, tissue mass 190 may be positioned on both frontal and dorsal sides of shield 140. As tissue mass 190 is being pulled from a location outside of inner tube 110 to a location within inner tube 110, tissue mass 190 is rotated via cutting edge 120. Rotated tissue mass 190 may become fragmented, cut, morcellated, into smaller tissue pieces 190A and 190B.

As shown in FIG. 3B, hooks 161 of tenaculum 160 grasps and pulls tissue mass 190 as cutting edge 120 cuts rotating tissue mass 190. As a surgeon pulls tenaculum 160, tenaculum 160 pulls the grasped tissue into inner tube 110 from inner tube's distal end 111 to proximal end 112. When cutting edge 120 is rotating and tenaculum 160 is moving, cutting edge 120 may be able to continuously cut tissue mass 190 into a continuous tissue peel, called "orange peeling." Once cut, the continuous tissue peel is removed from the inner tube's proximal end 112.

Figures 1, 10A:
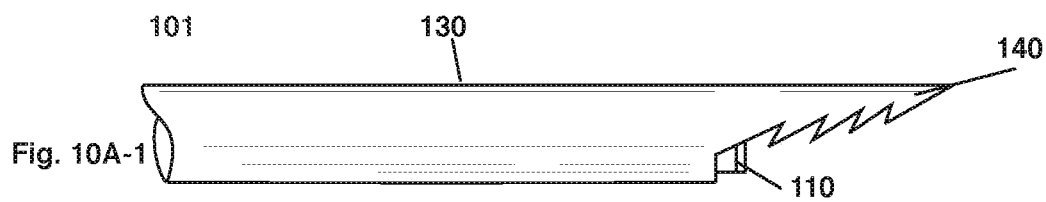
Figures 2, 10A:
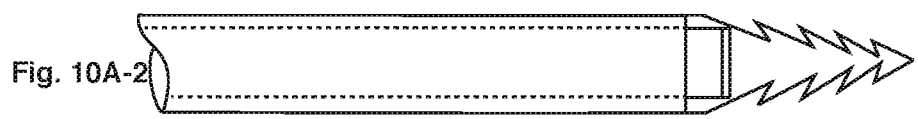

FIGS. 3C-1 and 3C-2 illustrate how during the second mode of operation, as tissue mass 190 is morcellated or cut by cutting edge 12, loose tissue pieces or fragments (hereinafter "loose tissue fragments 190a and 190b") are caught or trapped between arms 142 and/or notches 141 of shield 140. Accordingly, shield 140 limits or prevents loose tissue 190a and 190b from being displaced or disseminated within a patient's body. However, if a shield 140 with arms and/or notches is not positioned distal to cutting edge 120, then the loose tissue fragments may spin along with cutting edge and/or disseminate within the cavity. FIG. 3C-1 illustrates an internal view of tissue mass 190 traveling through inner tube 110, and FIG. 3C-2 illustrates an external view of the same.

FIG. 3D illustrates progressive pulling of the tissue mass 190 into inner tube's proximal end 112, leaving eventually only loose tissue fragments 190a and 190b captured in arms 142 and notches 141.

In embodiments, if arms 142 and notches 141 of shield 140 become saturated or filled with loose tissue, then morcellator 100 may be removed from the patient, and the loose tissue may be removed from the plurality of arms 142 manually or robotically. As shown in FIG. 3E, alternatively, loose pieces of tissue mass 190 may also be pulled into inner tube 110 via the pull force of tenaculum 160 as shown. In other embodiments, outer tube 130 may include a connection with a vacuum source to perform suction of loose tissue fragments, or a second outer tube may encase both tubes to connect with a vacuum source and perform suction. In another embodiment, a vacuum source may be connected the inner tube 110, or both the inner tube 110 and outer tube 130.

In embodiments the positions of shield's distal edge 140c, outer tube's distal end 131, and/or inner tube's distal end 111 may be fixed or adjustable. Distal edge 140c or the distal end of shield 140 may be curved or rounded to reduce the risk of the distal end or edge puncturing tissue.

FIGS. 4A-E illustrate how, in some embodiments, inner tube's distal end 111 and/or cutting edge 120 may be positioned at various locations: proximal or flush to outer tube's distal end (FIG. 4A), between shield's distal edge 140c and outer tube's distal end 131 (FIGS. 4B-4D), or distal to shield's distal edge 140c (FIG. 4E).

FIG. 4A illustrates an embodiment wherein inner tube's distal end 111 and/or cutting edge 120 is flush or adjacent to outer tube's distal end 131. In another embodiment, outer tubes distal end 131 may extend distally from inner tube's distal end 111 and/or cutting edge 120.

FIG. 4B-4D illustrates various embodiments wherein inner tube's distal end 111 and/or cutting edge 120 is positioned between shield's distal edge 140c and outer tube's distal end 131.

FIG. 4E illustrates an embodiment wherein inner tube's distal end 111 and/or cutting edge 120 is positioned distal to shield's distal edge 140c, though this position may limit the tissue catching ability of shield 140.

FIG. 4F illustrates that the possible positions of inner tube's distal end 111 and/or cutting edge 120 also applies to different shields, irrespective of shape and size.

In other embodiments, inner tube's distal end 111 and/or cutting edge 120 is configured to move along the longitudinal axis, such that an inner tube's distal end 111 may be positioned at any of the positions illustrated in FIGS. 4A-4E. In this embodiment, inner tube's distal end is configured to move along points proximal or distal to outer tube's distal end 131 and/or points proximal or distal to shield's distal edge 140c.

Figures 0, 16A:
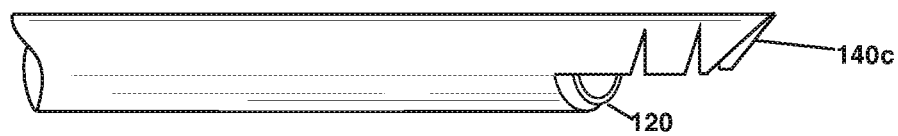
Figures 1, 16A:
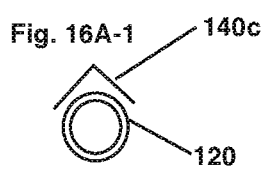
Figures 2, 16A:
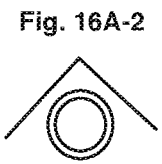
Figures 3, 16A:
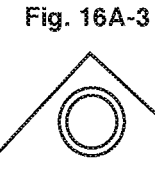

FIGS. 5A-1-5A-3 illustrates embodiments with alternative positions of shield 140, and in particular, alternative positions distal edge 140c in relation to inner tube's distal end 111 and outer tube's distal end 131. FIG. 5A-1 shows an embodiment where shield's distal edge 140c is positioned distal to both inner tube's distal end 111 and outer tube's distal end 131. FIG. 5A-2 shows an embodiment with a reduction in distance L4 between inner tube's distal end 111 and distal edge 140c. FIG. 5A-3 shows an embodiment where shield's distal edge 140c is positioned proximal to both inner tube's distal end 111 and outer tube's distal end 131, though this may reduce the tissue capturing efficacy of arms 142 and/or notches 141.

Other embodiments are also possible. For example, shield's distal edge 140c may be positioned proximal to inner tube's distal end 111 but distal to outer tube's distal end 131. Or, in embodiments where inner tube's distal end 111 is proximal to outer tube's distal end 131, shield's distal edge 140c may be positioned distal to inner tube's distal end 111 but proximal to outer tube's distal end 131.

Shield 140 may be configured to move along the longitudinal axis, such that distal edge 140c may be positioned at any of the points illustrated in FIGS. 5A1-5A3 or described above. For example, distal edge 140c may be configured to move along points proximal or distal to outer tube's distal end 131 and/or points proximal or distal to inner tube's distal end 111.

Shield 140 may also be retractable. As depicted in FIGS. 5A-3, shield 140 and outer tube 130 may be retracted from a position distal to cutting edge 120 to a position proximal to cutting edge 120, or any position in between. When shield 140 is proximal to cutting edge 120, cutting edge 120 may contract and cut tissue 190 before shield 610 contacts tissue 190. However, arms 142 of shield 140 may extend beyond the diameter of inner tube 110. Accordingly, arms 142 may still cut and catch tissue mass 190 while outer tube 130 is in the retracted position. FIG. 22-FIG. 26 describe retractable embodiments in greater detail.

FIGS. 5B1-5B3 show an embodiment of a sliding mechanism comprising a rail, track, spring, channel, passageway, track or slide 135 on outer tube 130, which enables shield 140 to slide along the longitudinal axis or outer surface of outer tube 130. Accordingly, a shield's distal edge 140c may be configured to slide along points proximal or distal to outer tube's distal end 131 and/or points proximal or distal to inner tube's distal end 111. Slide 135 may be a channel, passageway, etc. that is configured to allow shield 140 to independently move along a longitudinal axis of outer tube 130 and may be retractable itself.

FIG. 5B-1 illustrates a first position wherein distal edge 140c is distal to both inner tube's distal end 111 and outer tube's distal end 131. FIG. 5B-2 illustrates an intermediate position, and FIG. 5B3 illustrates a final position proximal to both inner tube's distal end 111 and outer tube's distal end 131. Embodiments may differ as to the range of positions permitted along the longitudinal axis. Sliding or retracting of distal edge 140c from a distal position to a more proximal position along a track or rail may be accomplished electronically, mechanically, or by simply pressing distal edge 140c against an organ, tissue, or object.

In other embodiments, outer tube 130 is configured to move along the longitudinal axis, such that outer tube's distal end 131 is positioned proximal or distal to inner tube's distal end 111. When outer tube 130 moves along the longitudinal axis, shield 140 correspondingly moves along the longitudinal axis if attached to the outer tube 130.

In other embodiments, inner tube's distal end 111 is positioned distal to shield's distal edge 140c, between shield's distal edge 140c and/or outer tube's distal end 131, or proximal to shield's distal edge 140c and/or outer tube's distal end 141.

FIGS. 6A-1 to 6F-2 depict a range of possible shapes of notch 141 configured to capture entrap loose tissue on shield 140. Generally, notch 141 may be shaped as any polygon, circle, or oval, in part or whole, or any combination, in part or whole, of a polygon, circle, and/or oval. A notch 141 may be shaped as a combination of multiple similar or dissimilar shapes. In addition, a notch 141 and may be defined by sidewalls that have composite similar or dissimilar shapes. Accordingly, a notch 141 may be symmetrical or asymmetrical to other notches 141 within a sidewall.

Figures 0, 16B:
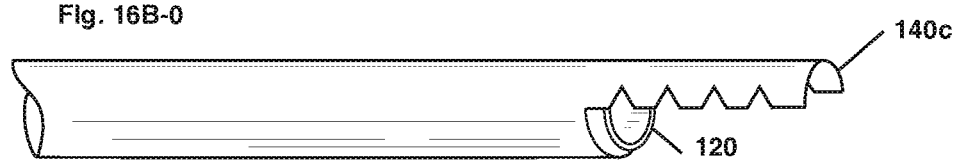
Figures 1, 16B:
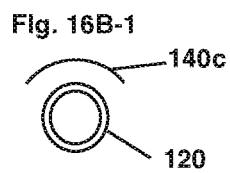
Figures 2, 16B:
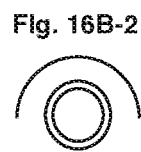
Figures 3, 16B:
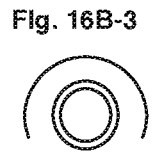
Figures 4, 16B:
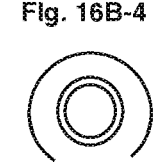

FIGS. 6A-1-6A-4 show a range of embodiments of notches 141 shaped as triangles, comprised of two sidewalls converging into an apex or point. Notch 141 may be shaped as an isosceles, acute, obtuse, equilateral, right or scalene triangle. FIG. 6A-1 is a notch 141 shaped as a simple isosceles triangle notch. FIGS. 6A-2 and 6A-3 are notches 141 shaped as obtuse triangles. 6A-4 is a notch 141 shapes as a triangle flanked by angled walls. Notch 141 may be triangular or "W", "V," "U" or "Z" shaped configured to assist in entrapping loose tissue outside of inner tube 110.

FIGS. 6B-1 to 6B-4 show a range of embodiments of polygonal and trapezoidal notches 141. FIG. 6B-1 is a notch 141 shaped as a simple square or rectangle. FIG. 6B-2 is a notch 141 shaped as a trapezoid. FIGS. 6B-3 and 6B4 illustrate a notch 141 shaped as portions of a hexagon. A notch 141 may be shaped as any polygon, trapezoid, or portion or combination of such shapes.

FIGS. 6C-1 and 6C-2 illustrate embodiments of a notch 141 shaped as a portion of a circle and oval, respectively. FIG. 6C-3 is a notch 141 shaped as a portion of a circle defined by sidewalls, which may also be shaped with portions of a circle. It can generally be appreciated that any notch 141 may be defined by sidewalls shaped by similar shapes or dissimilar shapes, as in FIG. 6C-3.

FIGS. 6D-1 to 6D-4 illustrate how embodiments of notches 141 may be comprised of or shaped as a combination of shapes previously described above (e.g., triangles, squares, rectangles, polygons, trapezoids, circles and ovals).

FIG. 6D-1 shows an embodiment of notch 141 shaped as three triangles to form a star-like notch 141. FIG. 6D-2 shows an embodiment of notch 141 shaped as a combination of a circle and a triangle. FIG. 6D-3 shows an embodiment of a notch 141 shaped as a trapezoid conjoined with a circle. FIG. 6D-4 shows an embodiment of a square notch defined by sidewalls comprised of a dissimilar shapes (in this case portions of circle).

A shield may be comprised of a singular notch 141 or a plurality of notches 141 distributed evenly or unevenly along all or a portion of the perimeter of shield 140. A perimeter may be defined by sidewall 140a, sidewall 140b, and distal edge 140c or it may be defined by a plurality of side walls. FIG. 6E-1 shows an embodiment of a series of identical notches 141 evenly distributed. FIG. 6E-2 shows an embodiment of a series of dissimilar notches 141. FIG.

6F-1 illustrates shows an embodiment of a series of notches 141 declining in size sequentially. FIG. 6F-2 shows an embodiment of a series of notches 141 distributed randomly in size.

Not all notches 141 need be dissimilar. For example, notches 141 may be shaped as a mixture right triangles or acute triangles. The right angle of notches 141 may be positioned more proximate to distal end of shield 140 than an acute angle of notches 141. The right triangles may be configured to assist in entrapping loose tissue outside of inner tube 110.

The sidewalls defining notches 141 may include grooves, slashes, zigzags, scores, etc. (referred to hereinafter individually and collectively as "grooves"), wherein grooves are be configured to assist in entrapping loose tissue outside of inner tube 110. Grooves may also be configured on any surface or portion of shield 140, inner tube 110 or outer tube 130, including their respective distal edges, and cutting edge 120.

One may appreciate that any shape which defines a notch 141 may also define an arm 142. For example, a sidewall containing two notches 141 defines an arm 142 between two notches 141 of the inverse shape. In other words, notches may create or define arms, and arms may create or define notches. Hence, the notches 141, as illustrated by FIGS. 6A-1-6F-2, may also define arms 142, and are illustrated as arms 142 in FIGS. 7A-1-7F-2.

FIGS. 7A-1 to 7F-3 depict a range of possible embodiments of an arm 142 configured to capture or entrap loose tissue on shield 140.

Generally, an embodiment of an arm 142 is shaped as any polygon, circle, or oval, in part or whole, or any combination, in part or whole, of a polygon, circle, and/or oval. Arm 142 may be shaped as a combination of multiple similar or dissimilar shapes. In addition, arm 142 and may be defined by sidewalls with similar or dissimilar shapes. Accordingly, an arm 142 may be symmetrical and/or asymmetrical to other arms 142 within a sidewall.

FIGS. 7A-1-7A-4 show embodiments of arms 142 shaped as triangles, comprised of two sidewalls converging into an apex. Arm 142 may be shaped as an isosceles, acute, obtuse, equilateral, right or scalene triangle, or any combination thereof. FIG. 7A-1 is an embodiment of an arm 142 shaped as a simple isosceles triangle notch. FIGS. 7A-2 and 7A-3 are embodiments of arms 142 shaped as obtuse triangles. FIG. 7A-4 is an embodiment of arm 142 shapes as a triangle flanked by angled walls. Generally, arms 142 may be triangular or "V", "W," "U" or "Z" shaped configured to assist in entrapping loose tissue outside of inner tube 110.

FIGS. 7B-1 to 7B-4 show embodiments of polygonal and trapezoidal arms 142. FIG. 7B-1 is an embodiment of arm 142 shaped as a simple square or rectangle. FIG. 7B-2 is embodiment of an arm 142 shaped as a trapezoid. FIGS. 7B-3 and 7B4 illustrates an embodiment of arm 142 shaped as portions of a hexagon. An arm 142 may be shaped as any polygon, trapezoid, or portion(s) or combination of such shapes.

FIGS. 7C-1 and 7C-2 illustrate an embodiment of arm 142 shaped as a portion of a circle and oval, respectively. FIG. 7C-3 is an embodiment of arm 142 shaped as a portion of a circle defined by sidewalls, which may also be shaped with a portion of circle. It can generally be appreciated that any arm 142 may be defined by sidewalls shaped by similar shapes or dissimilar shapes, as in FIG. 7C-3.

FIGS. 7D-1 to 7D-4 illustrate how embodiments of arms 142 may be comprised of or shaped as a combination of shapes previously described above (e.g., triangles, squares, rectangles, polygons, trapezoids, circles and ovals).

FIG. 7D-1 shows an embodiment of arm 142 shaped as three triangles form a star-like arm 142. FIG. 7D-2 illustrates an embodiment of arm 142 shaped as a combination of a circle and a triangle. FIG. 7D-3 illustrates an embodiment of arm 142 shaped as a trapezoid conjoined with a circle. FIG. 7D-4 illustrates an embodiment of a square arm defined by sidewalls with dissimilar shapes (in this case portions of circle).

Embodiments of a shield may be comprised of a singular notch or a plurality of arms 142 distributed evenly or unevenly along all or a portion of the perimeter of shield 140, such perimeter being defined by sidewall 140a, sidewall 140b, and distal edge 140c. FIG. 7E-1 shows an embodiment of a series of identical arms 142 evenly distributed. FIG. 7E-2 shows an embodiment of a series of dissimilar arms 142. FIG. 7F-1 illustrates an embodiment of a series of arms 142 declining in size sequentially. FIG. 7F-2 illustrates an embodiment of a series of arms 142 distributed randomly in size.

Not all arms 142 need be dissimilar. For example, arms may be shaped as right triangles or acute triangles. The right angle of arms 142 may be positioned more proximate to distal end of shield 140 than an acute angle of arms 142. The right triangles may be configured to assist in entrapping loose tissue outside of inner tube 110.

The sidewalls defining arms 142 may include grooves configured to assist in entrapping loose tissue outside of inner tube 110.

FIGS. 8A-1 to 8F-3 illustrate plan views of embodiments of a shield 140, and further illustrate possible configurations and positions of arm(s) 142 and notch(es) 141 along the perimeter of shield 140. For the purposes of illustration, notch(es) 141 are generally shaped as portions of circle or a triangle. It should be appreciated however than any shape previously described, illustrated or conceived or useful for capturing loose tissue may be utilized.

FIG. 8A-1 illustrates an embodiment wherein notches 141 and arms 142 are symmetrically placed along sidewalls 104b and 140a, and are of same or similar shape and size. FIG. 8B-1 illustrates an embodiment of a shield 140 containing a single notch on first and second sidewalls 140a and 140b. FIG. 8C-1 illustrates an embodiment of a shield 140 wherein notches 141 and arms 142 are integral or part of distal edge 104c. FIG. 8D-1 illustrates an embodiment wherein notch (es) 141 and arms 142 are asymmetric on sidewalls and/or unevenly distributed along sidewalls. FIG. 8D-1 illustrates an embodiment wherein the number of notches 141 and arms 142 on a first sidewall are not equal the number of notches 141 and arms 142 on a second sidewall. FIG. 8E-1 shows an embodiment where a plurality of notches 141 and arms 142 form either sidewall. FIG. 8F-1 illustrates an embodiment where notches 141 and arms 142 on sidewalls are of different size and shape, are defined by smaller shapes and are unevenly distributed. It should be appreciated that the variations described above are applicable to embodiments with a plurality of sidewalls and embodiments of different shield shapes and sizes.

Although notches 141, arms 142, and grooves, etc. depicted in FIGS. 8A-1 to 8F-1 are depicted on both sidewalls 140a and 140b of a shield 140, it will be appreciated that notches 141, arms 142, and grooves may be positioned on only a single side of a shield as shown in complementary FIGS. 8A-2 to 8F-2.

FIGS. 8A-3 to 8F-3 illustrate that a distal edge 140c of a symmetric or asymmetric shield may also include one more notches 141 and arms 142.

Any configuration of notches 141 and arms 142 described or illustrated with respect to a sidewall of shield 140 is also be applicable to outer tube's distal edge 131, inner tube's distal edge 111, cutting edge 120, distal edge 140c, or any edge on a morcellation device. For examples, FIG. 8A-3 illustrates that notches 141 and arms 142 on distal edge 104c may be different in shape and size than those on the sidewalls. FIG. 8B-3 shows that embodiments with one or more notches 141 and/or arms 142 on only one sidewall may contain one or more notches 141 and/or arms 142 on distal edge 104c. FIG. 8C-3 illustrates that arms 142 and notches 141 may be not clearly located on either a sidewalls 140a or 140b or distal edge 140c but rather may form contiguously. FIG. 8D-3 illustrates that arms 142 and notches 141 may be unevenly distributed on distal edge 140c. FIG. 8F-3 illustrates that notches 141 and arms 142 on distal edge 140c may be defined by a combination of shapes.

FIGS. 9A-1 to 9I-3 illustrate examples of embodiments of a denticulate shield 140 or a portion of denticulate shield 140 configured for capturing loose tissue. Any shape or combination of shapes described above may be substituted. As shown in the Figures, shield 140 may have a finger, comb or rake-like structure with arms 142 separated by notches 141. The rake-like structure may have a plurality of arms 142 and/or notches 141, wherein notches 141 may be orifices between arms 142. Notches 141 and/or arms 142 may be configured to catch loose, morcellated tissue that is cut by cutting edge 120. Additionally, notches 141 and/or arms 142 may be configured to limit, prevent, or reduce the morcellated tissue from being repositioned within the patient.

As shown, arms 142 may have different lengths and/or sizes. However, in other embodiments arms 142 may have symmetrical lengths and sizes. Arms 142 may have spear like structures, wherein the length of arms 142 diminishes toward the end of shield 140.

FIGS. 9A-1 and 9A-2 shows a perspective and plan view respectively of a symmetrical shield containing square notches 141 and arms 142 along sidewalls 140a and 140b, and a curved or rounded distal edge 140c for atraumatic contact with tissue.

FIGS. 9B-1 through 9D-1 show perspective views of symmetrical and asymmetrical shields with one or more notches 141 shaped as a "V" or triangles configured for capturing loose tissue with a curved or rounded distal edge 140c for atraumatic contact with tissue. FIGS. 9B-2 through 9D-2 show plan views respectively.

FIGS. 9E-1 and 9E-2 show a perspective and plan view respectively of FIGS. 9C-1 and 9C-2 with an angled distal edge 140c, rather than a curved or rounded edge.

FIGS. 9F-1 and 9F-2 show a perspective and plan view respectively of a shield with sidewalls 104a and 104b formed in a zigzag or tree like configuration to capture loose tissue. Distal edge 140c may be pointed, as illustrated, or curved or rounded for an atraumatic design.

FIGS. 9G-1 through 9I-1 show perspective views of an embodiment of a shield with sidewalls containing similar notches 141 shaped as a combination of a circle and triangle. FIGS. 9G-2 through 9I-2 show the respective plan views. As shown, the plurality of notches 141 forming arms 142 may extend across sidewalls 140a and 140b of shield 140. The plurality of notches 141 may have symmetrical shapes with a wide base and a narrow apex. The symmetrical shapes may include angled edges, wherein the bases are positioned on the sidewalls of shield 140 and the apexes are positioned closer to the midline or center of shield 140. The apexes may include cylindrical holes. The angled edges forming notches 141 may be configured to guide morcellated tissue to the cylindrical hole, wherein the cylindrical hole may secure the loose tissue.

FIG. 9G-1 illustrates a curved or rounded distal edge 140c, whereas 9H-I and 9I-1 illustrate a triangular shaped distal edge 140c. 9I-1 illustrates how sidewalls may also be angled to further make shield 140 more triangular shaped, as evident from plan view 9I2, wherein sidewalls are angled to have a longer perimeter at a proximal end and a shorter perimeter at a distal end.

FIGS. 9H-2 and 9I-3 show plan views of embodiments with more blunted or curved arms 142 to minimize trauma to tissue.

FIGS. 10A-1-10D-2 illustrate embodiments of a shield integrated with a morcellator distal end 101, and in particular outer tube 130. FIGS. 10A-1 and 10A-2 show a side and plan view respectively and shield illustrated in FIG. 9F-1 integrated with outer tube 130.

Figures 1, 10B:
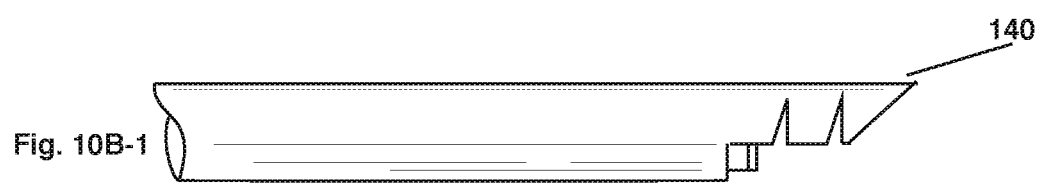
Figures 2, 10B:
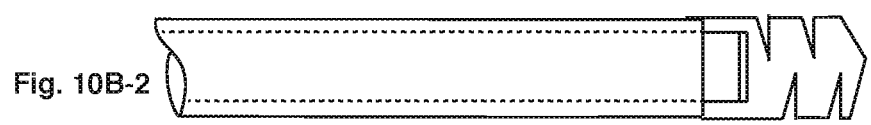

FIGS. 10B-1 and 10B-2 show a side and plan view respectively and shield illustrated in FIG. 9E-1 integrated with outer tube 130.

Figures 1, 10C:
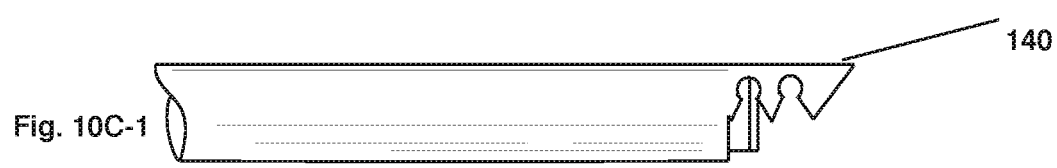
Figures 2, 10C:
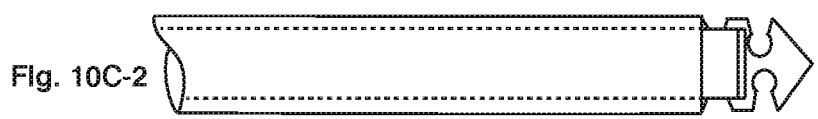

FIGS. 10C-1 and 10C-2 show a side and plan view respectively and shield illustrated in FIG. 9I-1 integrated with outer tube 130, wherein shield 140 is a triangular or spear like structure, narrowing from a proximal to the distal tip to form a point.

Figures 1, 10D:
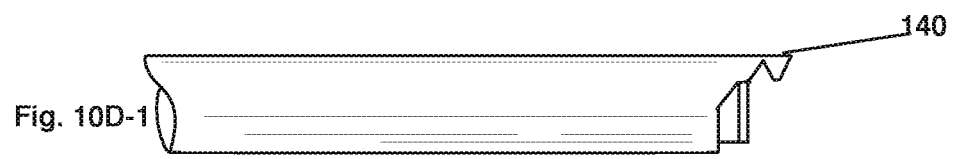
Figures 2, 10D:

FIGS. 10D-1 and 10D-2 show a side and plan view respectively and shield containing a single "V" notch 141 on either sidewalls 140a and 140b.

Figure 11A:
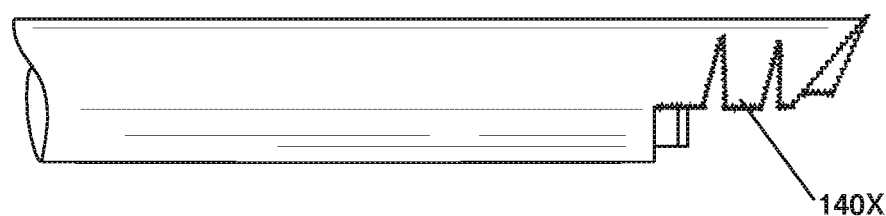
FIGS. 11A, 11B, 11C, 11D, 11E, 11F, 11G, 11H, 11I, 11J depict serration embodiments for a morcellator.
Figure 11B:
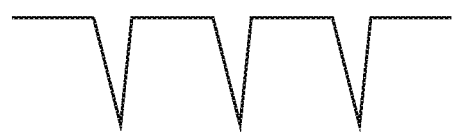
Figure 11D:
Figure 11F:
Figure 11I:
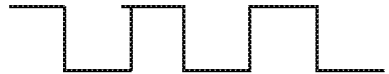
Figure 11C:
Figure 11E:
Figure 11G:
Figure 11H:
Figure 11J:
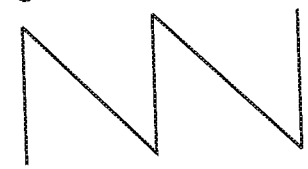

FIG. 11A illustrates a serrated denticulate shield 140. Serrations 14 may be along all or a portion of sidewalls and distal edge 140c of shield 140's perimeter. Serrations 14 may be in a series of "V" (FIGS. 11B, 11C, 11D, 11F, 11J), "Z", zigzags, mixed shapes (FIG. 9E), circles (FIG. 11G), squares (FIG. 11I), randomly shaped wedges (FIG. 11E, 11J) or any other shape that achieves a gripping effect.

FIGS. 12A-1 to 12H-1 illustrate plan view perspectives of possible shapes of a denticulate shield 140 configured for catching tissue. The perimeter of shield 140 is dotted so as to indicate that any configuration of notches 141 and arms 142 previously described, illustrated or useful for catching tissue may be added. For illustrative purposes, FIGS. 12A-2 to 12H-1 illustrate possible embodiments FIGS. 12A-1 to 12H-1 respectively containing arms 142 and notches 141.

FIGS. 12A-1 and 12A-2 illustrate a plan view of morcellator 100, wherein a shield 140 is shaped as a spear head. FIGS. 12B-1 through 12H-1 illustrate a plan view of morcellator 100, wherein a shield is shaped as a complete or partial oval, square, triangle, spear, hexagon, trapezoid, and mixed circle and trapezoid shape respectively. In general, a shield 140 may be formed by a plurality of sidewalls and edges with arms 142 and/or notches 141. FIGS. 12A-1 to 12H-1 showing respective embodiments illustrate how the shape may be altered with the addition of including arms 142 and notches 141, through the generalized shape holds.

Figures 1, 13A:
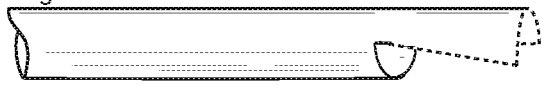
Figures 2, 13A:
Figure 13:
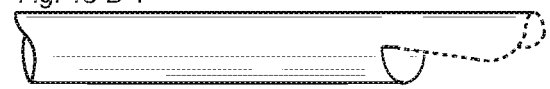
FIGS. 13-A1, 13-A2, 13-B1, 13-B2, 13-C1, 13-C2, 13-D1, 13-D2, 13-E1, 13-E2, 13-F1, 13-F2, 13-G1, 13-G2, 13-H1, 13-H2, 13-I1, 13-I2 depict perspective views of various shield shapes.
Figure 13:
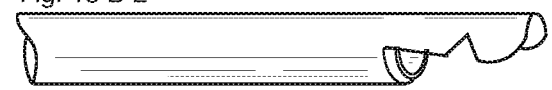
Figures 1, 13C:
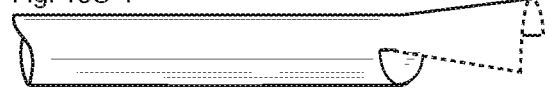
Figures 2, 13C:
Figures 1, 13D:
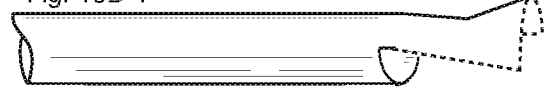
Figures 2, 13D:
Figures 1, 13E:
Figures 2, 13E:
Figures 1, 13F:
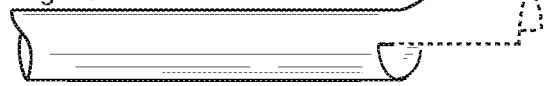
Figures 2, 13F:
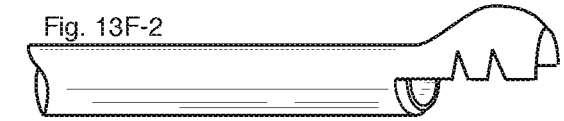
Figures 1, 13G:
Figures 2, 13G:
Figures 1, 13H:
Figures 2, 13H:
Figures 1, 13I:
Figures 2, 13I:

FIGS. 13A-1 to 13I-1 illustrate perspective views of generalized shapes of shield 140 configured for catching tissue. The perimeter of shield 140 is dotted so as to indicate that any configuration of notches 141 and arms 142 previously described, illustrated or useful for catching tissue may be configured. It may also be appreciated that the shapes illustrated may also apply to embodiments containing more than 2 sidewalls.

For illustrative purposes, FIGS. 13A-2 to 13I-2 illustrate embodiments of FIGS. 13A-1 to 13I-1 respectively containing arms 142 and notches 141 and configured for attachment to outer tube 130. However, embodiments of shield 140 shown in FIGS. 13A-1 to 13I-2 may attach to inner tube 110 or other tubes or parts associated with a morcellator.

FIGS. 13A-1 and 13B-1 illustrates an embodiment wherein sidewalls 140*a* and 140*b* of shield 140 slope downward towards the axis of rotation, increasing the perimeter of distal edge 140*c* and thereby creating portions of a cone. FIG. 13A-1's sidewalls and distal edge 140*c* intersects at a sharp angle, whereas FIG. 13B-1 has a continuous curvature for atraumatic manipulation. Generally, any embodiment of shield 140 illustrated may have a continuous curvature for atraumatic manipulation.

FIG. 13C-1 illustrates an embodiment wherein sidewalls 140*a* and 140*b* of shield 140 slope downward and an upper surface of shield slopes upward so that a radius of shield 140 exceeds the radius of outer tube 130 and inner tube 110. This embodiment may also create a portion of a cone. In other words, shield 140 has a proximal arc and a distal arc, wherein the distal arc is greater than the proximal arc.

FIG. 13D-1 illustrates an embodiment wherein a portion of shield 140 between sidewalls 104*a* and 104*b* slopes upward between the proximal and distal ends of the sidewall to create a kink.

FIG. 13E-1 illustrates an embodiment wherein a portion of shield 140 between sidewalls 104*a* and 104*b* curve downward and then upward between the proximal and distal ends of the sidewall to create a concave shield. FIG. 13E-2 also shows an embodiment where the body of the shield is curved with respect to the axis of rotation of the inner tube 110 and cutting edge 120.

FIG. 13F-1 illustrates an embodiment wherein a portion of shield 140 between sidewalls 104*a* and 104*b* curve upward and then downward between the proximal and distal ends of the sidewall to create a convex shield. FIG. 13F-2 also shows an embodiment where the body of the shield is curved with respect to the axis of rotation of the inner tube 110 and cutting edge 120. In this embodiment, shield 140 has a proximal arc and a distal arc, wherein the distal arc is greater than the proximal arc.

FIG. 13G-1 illustrates an embodiment wherein sidewalls 140*a* and 140*b* of shield 140 slope upward away from the axis of rotation, decreasing the perimeter of distal edge 140*c* and thereby creating a portion of a cone.

FIG. 13H-1 illustrates an embodiment wherein a first portion of sidewalls 104*a* and 104*b* are linear and parallel, and a second portion of shield 140 between sidewalls 104*a* and 104*b* slopes downward between the proximal and distal ends of the sidewall to create a kink-like effect.

FIG. 13I-1 illustrates an embodiment wherein the top portion of shield 140 and sidewalls 104*a* and 104*b* slope parallel and upward between the proximal and distal ends of the sidewall. In another embodiment, shield 140 may be in a first position as shown in FIG. 13A-1, and be able to move to a second position as shown in FIG. 13I-2, for example, when morcellating a large tissue mass 190. The movement from a first to second position may be accomplished by a hinge or latch.

Figures 1, 14A:
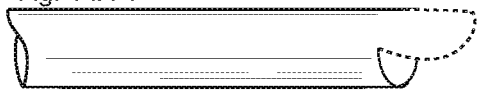
Figures 2, 14A:
Figures 1, 14B:
Figures 2, 14B:
Figures 1, 14C:
Figures 2, 14C:
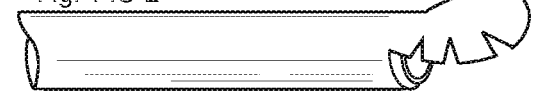
Figures 1, 14D:
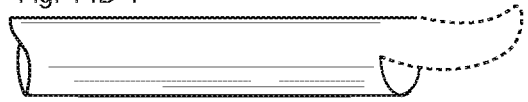
Figures 2, 14D:
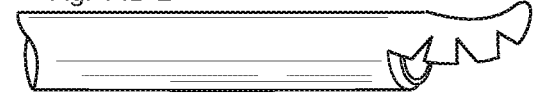
Figures 1, 14E:
Figures 2, 14E:

FIGS. 14A-1 and 14E-1 illustrate perspective views of possible shapes of shield 140 configured for catching tissue wherein shield 140 includes no sharp angles along the perimeter but is instead contiguous and curved (though angled sidewalls may be added). The perimeter of shield 140 is dotted so as to indicate that any configuration of notches 141 and arms 142 previously described, illustrated or useful for catching tissue may be added.

FIGS. 14A-2 to 14E-2 illustrate possible configurations containing arms 142 and notches 141 and configured for attachment to outer tube 130. However, in other embodiments of shield 140 shown in FIGS. 14A-1 to 14E-2 the shield may attach to inner tube 110 or other tubes or parts associated with a morcellator.

Figures 1, 15A:
Figures 2, 15A:
Figures 1, 15B:
Figures 2, 15B:
Figures 1, 15C:
Figures 2, 15C:
Figures 1, 15D:
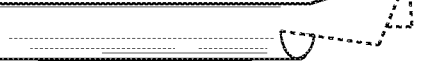
Figures 2, 15D:
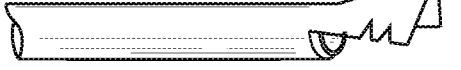
Figures 1, 15E:
Figures 2, 15E:
Figures 1, 15F:
Figures 2, 15F:
Figures 1, 15G:
Figures 2, 15G:
Figures 1, 15H:
Figures 2, 15H:

FIGS. 15A-1 and 15H-1 illustrate perspective views of possible shapes of shield 140 configured for catching tissue wherein shield's sidewalls 104*a* and 104*b* converge to form a triangle point or apex. The perimeter of shield 140 is dotted so as to indicate that any configuration of notches and arms 142 previously described, illustrated or useful for catching tissue may be added. For illustrative purposes, FIGS. 15A-2 to 15H-2 illustrate embodiments of FIGS. 15A-1 and 15H-1 configured for coupling or attachment to outer tube 130. However, embodiments of shield 140 shown in 15A-1 and 15H-1 may also attach to inner tube 110 or other tubes or parts associated with a morcellator.

FIGS. 16A-0 illustrates a side view of an embodiment wherein shield 140 has a peaked structure, creating an angled roof over cutting edge 120 with two or more sidewalls meeting at an angle or a point. FIGS. 16A-1 through 16A-3 show that shield 140 may extend around cutting edge 120 in different portions around cutting edge 120's circumference: partially (¼ or less) (FIG. 16A-1), half way (FIG. 16A-2), or covering most of the cutting edge's circumference (FIG. 16A-3).

FIGS. 16B-0 illustrates a side view of an embodiment wherein shield 140 is curved, FIGS. 16B-1 through 16B-3 show possible front views and in particular that shield 140 may curve around cutting edge in different portions: partially (¼ or less) (FIG. 16B-1), half way around (FIG. 16B-2), three-quarters (FIG. 16B-3) or covering most of the cutting edge's circumference (FIG. 16B-4).

In another embodiment, shield 140 has a curvature that is substantially similar to outer tube 130, wherein a first set of arms 142 extends towards a first side of outer tube 130 and a second set of arms 142 extends towards a second side of outer tube 130. By shield 140 having arms 142 that project in both directions, the surface area of shield 140 increases, which may allow shield 140 to catch more loose tissue fragments.

Figure 17A:
FIGS. 17A, 17B, 17C, 17D, 17E, 17F, 17G, 17H depict exemplary attachments of a shield to a morcellator.
Figure 17B:
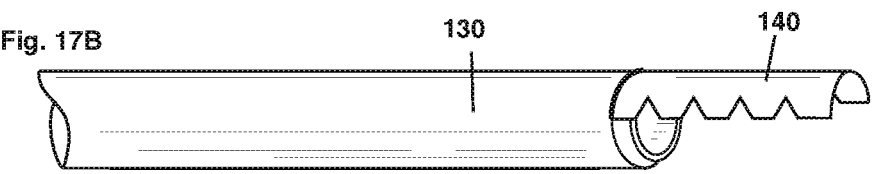
Figure 17C:
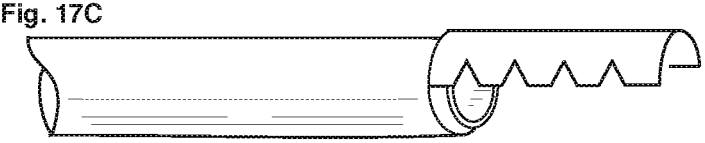

FIGS. 17A through 17H show possible attachments 180 of a shield 140 to a morcellator 100. In an embodiment, Shield 140 is fixedly coupled to distal end 131 of outer tube 130, such that outer tube 130 and shield 140 form a unitary piece. In another embodiment, shield 140 forms a continuous part of the morcellator. For example, shield 140 may be integral, a part of, or an extension of outer tube 130 as shown in FIG. 17A. In embodiments, shield 140 may be affixed via adhesion, gluing, welding or any other affixation method to outer tube 130 as shown in FIG. 17B. Shield 140 may have the same diameter morcellator's outer tube 130 as shown in FIG. 17A, or be a slightly smaller or larger circumference as shown in FIG. 17C.

Shield 140 may be comprised of plastic, metal, or any other desired, relatively stiff material. In embodiments, to maintain sufficient stiffness and strength, shield 140 may not be configured to rotate or hinge around an axis. However, in other embodiments, shield 140 may be rotated or hinged around an axis.

Figure 17D:
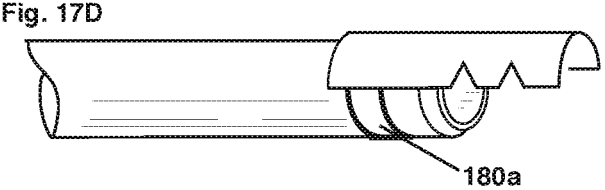
Figure 17E:
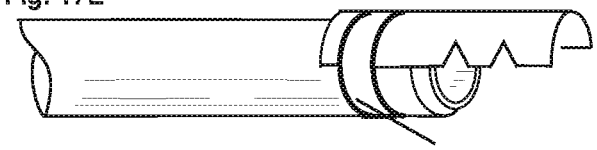
Figure 17F:
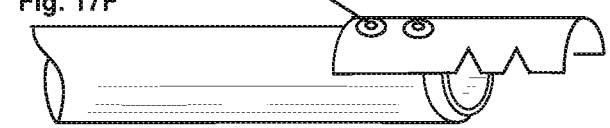
Figure 17G:
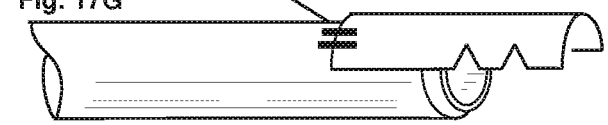

Shield 140 may be affixed, strapped, or tied to outer tube by a portion of shield 140's circumference as shown in FIG. 17D or all of shield 140's circumference as shown in FIG. 17E via a strap, string, or mounting sleeve 180*a*. Materials may include but are not limited to Velcro, metal, plastics, or fibrous materials. Shield 140 may be affixed via nails 180*c*

Figure 17H:
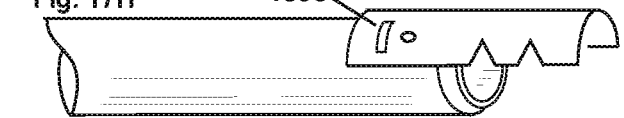

(FIG. 17F), tape 180d (FIG. 17G), or an alternative connecting method such as staples, welds, mounting sleeves, fasteners, or riveted attachments (FIG. 17H).

Figures 1, 18A:
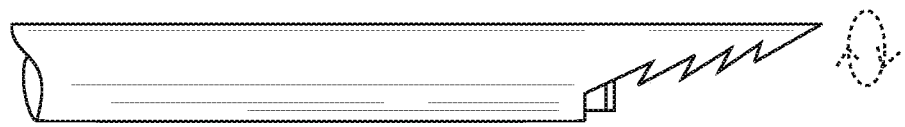
Figures 2, 18A:
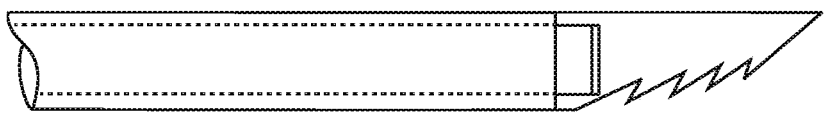
Figures 1, 18B:
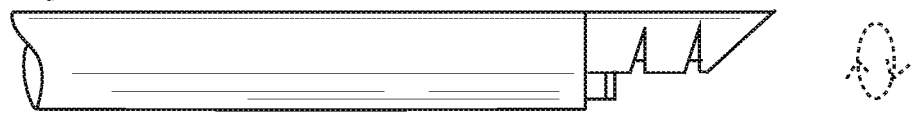
Figures 2, 18B:
Figures 1, 18C:
Figures 2, 18C:

FIGS. 18A-1 through 18A-3 illustrate side views embodiment of a morcellator containing notches 141 and arms 142 only on one portion or one sidewall of shield 140. FIGS. 18B-1 through 18B-3 illustrate bottom views of the respective embodiments. In embodiments wherein arms 142 and notches 141 are positioned on only one sidewall or a portion of the shield 140, arms 142 and notches 141 may be tangentially facing or directed towards a direction of rotation of inner tube 110. For example, the embodiments show a clockwise rotation with notches 141 and arms 142 positioned between 7 'o clock and 11 o'clock and facing counterclockwise oncoming tissue rotation. Alternatively, if the embodiment rotates counter-clockwise, arms 142 and/or notches 141 could be positioned between 1 o'clock and 5 o'clock and face clockwise. Therefore, as inner tube 110 rotates, the sidewall with arms and notches may catch morcellated tissue that are rotating along with inner tube 110.

FIGS. 19A through 19C show that a distal portion of a shield that includes a knot, mass, or knob 149 to facilitate peeling of tissue during morcellation. In addition, FIG. 19A illustrates an embodiment of shield having a curvature or nose sloping downward between the shield's distal and proximal end.

FIGS. 19C and 19D illustrates an embodiment wherein a shield 140 includes a rim 140r around part or all of the shield's perimeter so as to be atraumatic to tissue within the patient. FIGS. 19F-1 to 19F-3 offer views looking from a proximal end of shield 140 to a distal end, and in particular showing a curved or rounded rim embodiment 140r along distal edge 140c. FIGS. 19G and 19H respectively show perspective views of shield 140 showing a rim 140r on distal edge 140c and a rim 141r around a notch 141.

FIGS. 20A-20C illustrate a perspective, bottom and side views respectively of another embodiment wherein shield 140 is attached or extends from inner tube 110. In this embodiment, inner tube's tube distal end 111 is coupled both to shield 140 and cutting edge 120, which extends distally past outer tube's distal end 131. All previous descriptions and configurations describing arms, notches, shield shapes, etc. and the relationship of shield 140 to outer tube 130 may also describe the relationships between shield 140 and inner tube. For example, inner tube 110 and/or shield 140 may also be retractable or may be fixed in alternative position with respect to outer tube 130.

Figure 21A:
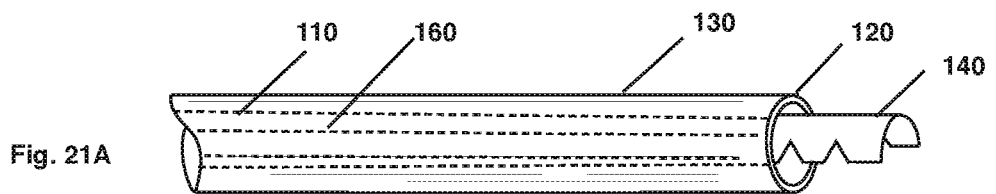
FIGS. 21A-21B illustrate views of another embodiment wherein shield is coupled to an inner tube of a morcellator and the outer tube has a cutting edge.
Figure 21B:
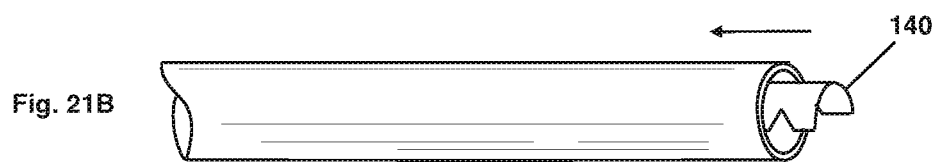

FIGS. 21A-21B illustrate a view of an another embodiment wherein shield 140 is attached to or extends from inner tube 110 and outer tube 130 and has a cutting edge 120. All previous descriptions and configurations describing arms, notches, shield shapes, etc. may also apply in this embodiment. In this embodiment, outer tube's distal end 131 may be proximal, distal or flush with inner tube's distal end 111, or may be slideable between all or a subset of positions. All previous descriptions and configurations describing the relationship of shield 140 to outer tube 130 may also describe the relationships between shield 140 and inner tube. For example, inner tube and shield may also be retractable.

Outer tubes and/or inner tubes may also be added to all other embodiments described or illustrated in this specification. These include embodiments wherein shield 140 is coupled to outer tube 130 and an inner tube 110 of lesser diameter is coupled to a cutting edge 120. Outer and inner tubes may also be added to an embodiment wherein shield 140 and cutting edge are coupled to inner tube 110 of lesser diameter than outer tube 140, which may or may not also have an additional cutting edge 140. Outer and/or inner tubes may also be added to embodiments wherein shield 140 and a cutting edge 140 are couple to outer tube 130.

Figure 21C:
FIGS. 21C, 21D, 21E illustrate views of another embodiment of a morcellator with an additional outer tube.
Figure 21D:
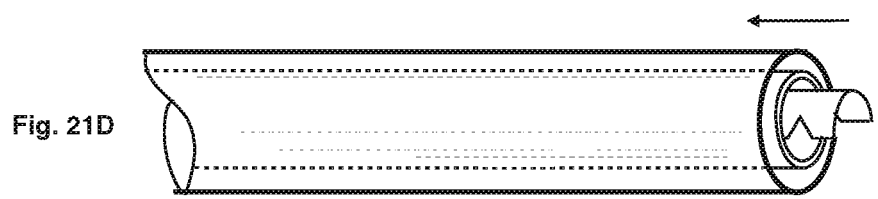
Figure 21E:
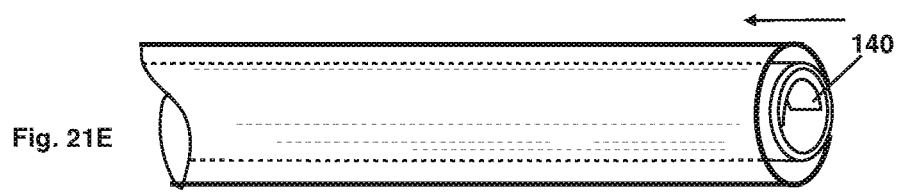

For example, FIG. 21C shows an additional outer tube 150 added to the embodiment shown in FIGS. 21A and 21B. FIGS. 20D and 20E illustrate an embodiment wherein the shield 140 is retractable. This may be accomplished, for example, by a slide, rail or spring mechanism.

In some embodiments, an additional tube serves a suction and/or irrigation function. For example, an additional outer and/or inner tube may be attached to a suction or vacuum source and/or irrigation source that permits a surgeon to suction fragments for example captured on a shield.

FIG. 22 illustrates an embodiment of shield 140 wherein shield 140 is coupled or integrated with a retractable outer tube 130, which retracts responsive to distal edge 140c of shield 140 pressing against a tissue mass 190. In this embodiment, shield 140 and outer tube 130 are in a starting position before making contact with tissue mass 190. Upon contacting tissue mass 190, outer tube 130 and attached shield 140 retract to a second position reducing distance L4 between inner tube's distal end 111 and shield's distal edge 140c. Shield distal edge 140c may as result of retraction be in a second position distal to cutting edge 120 (FIG. 22B), flush or adjacent with cutting edge (FIG. 22C), or proximal to cutting edge (FIG. 22D). As tissue mass 190 is further morcellated, however, length L4 increases (FIG. 22E) and shield 140 eventually returns to the shield's first position (FIG. 22F). An advantage of this press retraction embodiment is that it permits cutting edge 120 to morcellator tissue without interference of shield 140 until the mass has been diminished in size, precisely the moment when stray tissue pieces are formed by cutting edge 120 and disseminated. Tissue pieces are generated typically at the end of morcellating a large mass, so shield 140 serves its tissue capturing function when tissue mass 190 has reduced in size substantially.

Figure 23A:
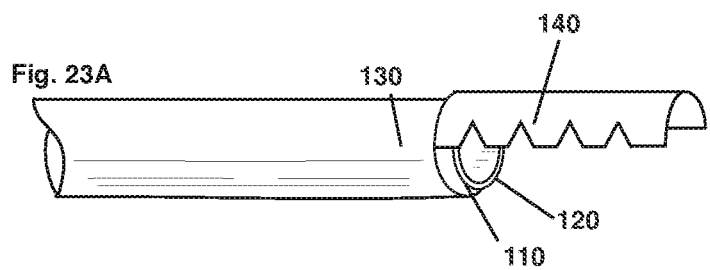
FIGS. 23A, 23B, 23C, 23D, 23E illustrate an another embodiment of a morcellator wherein the outer tube is stationary with respect to inner tube and only the shield is retractable.
Figure 23B:
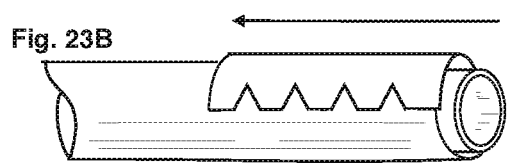
Figure 23C:
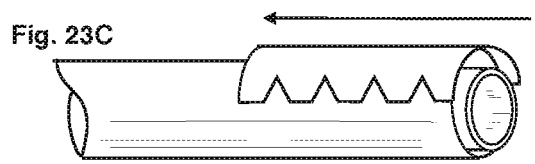
Figure 23D:
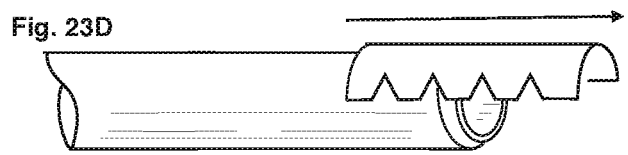
Figure 23E:
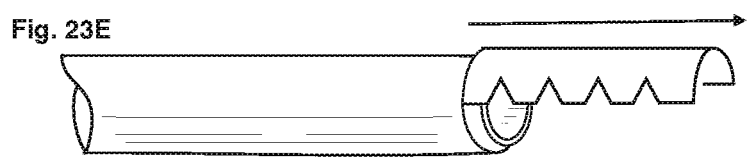
Figure 24A:
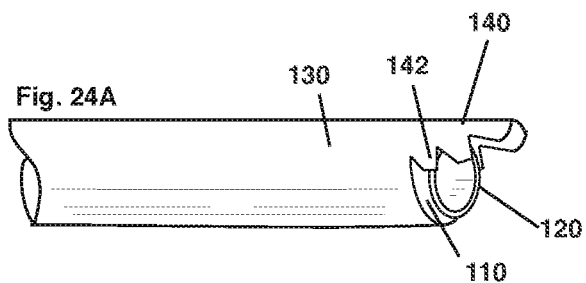
FIGS. 24A, 24B, 24C, 24D illustrate an embodiment of a morcellator wherein the shield and outer tube are a single, integrated and retractable piece.
Figure 24B:
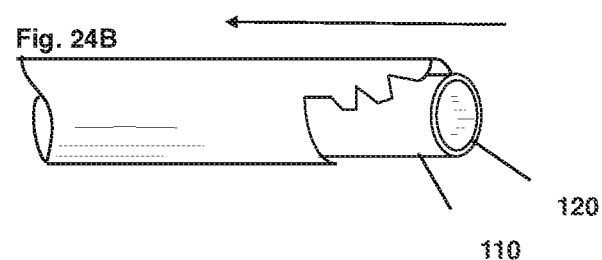
Figure 24C:
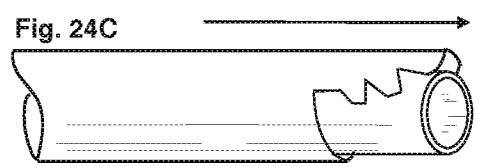
Figure 24D:
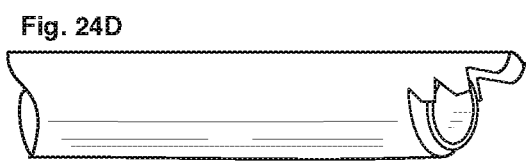

FIGS. 23A through 23E illustrate an another embodiment of a retractable shield 140 wherein outer tube 140 is stationary with respect to inner tube 110 and only shield 140 is retractable. Like the embodiment of FIGS. 22A through F, upon contacting tissue mass 190, shield 140 retracts to a second position. Shield's distal edge 140c may as result of retraction be in a second position distal to cutting edge 120 (FIG. 23B), flush with cutting edge (FIG. 23C), or proximal to cutting edge (FIG. 23C). As tissue mass 190 is further morcellated, however, shield 140 eventually returns to the first position (FIG. 23E). An advantage of this press retraction embodiment is that it permits cutting edge 120 to morcellate tissue without interference of shield 140 until mass 190 has been diminished in size, precisely the moment when stray tissue pieces are formed by cutting edge 120 and disseminated.

FIGS. 24A through 24D illustrate an embodiment wherein shield 140 and outer tube 130 are a single, integrated and retractable piece. Like FIG. 22, this embodiment is able to retract to a second position upon contact with a tissue mass 190 and returns to the shield's starting position as tissue mass 190 decreases in size. This embodiment has a curved distal shield edge 140s with upward sloping curved walls and triangle notches. This embodiment illustrates that shields may include the space, notch, curvature and general shape variations described through the specification.

Figure 25A:
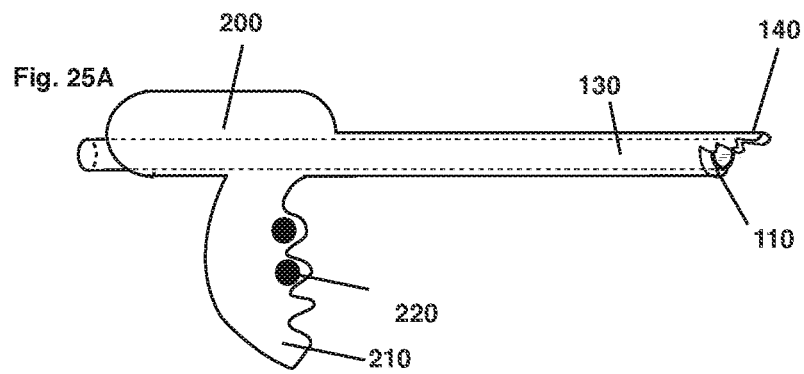
FIGS. 25A, 25B, 25C, 25D illustrate an embodiment of a morcellator including a hand grippable body and handle.
Figure 25B:
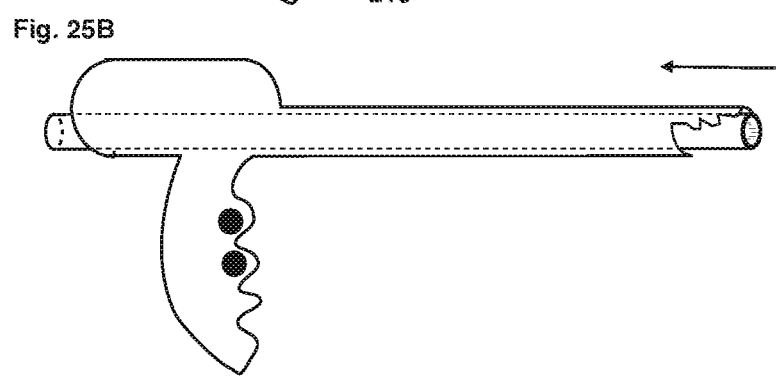
Figure 25C:
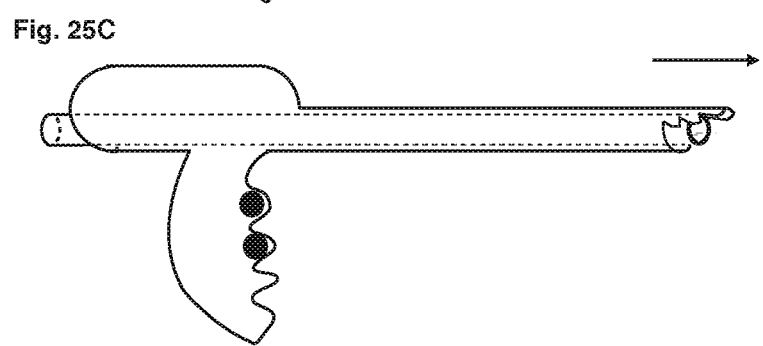
Figure 25D:
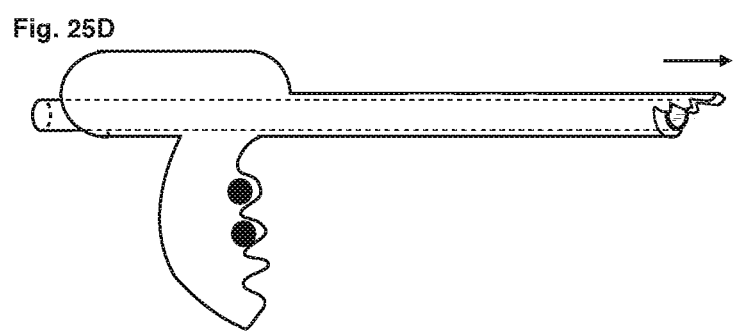

FIGS. 25A through 25D illustrate an embodiment of a morcellator device including a hand grippable body 210 and handle 200. Handle 200 may include components such as a motor, rotating drum or wheel for rotating the cutting edge rotate and spin and also mechanisms that automate retraction of shield 140 and/or outer tube 130. For example, handle 200 may include buttons 220 that permit a surgeon to start rotation of cutting edge 120 for morcellation (e.g., rotation of inner tube 110 and cutting edge 120) and/or electronic retraction of shield 140 (though the retraction may be accomplished through mechanical and press forces described in earlier embodiments). For example, one button may control the position of shield 140 with respect to the cutting edge 140c or inner tube (retraction). Another button may control the speed of morcellation (e.g., speed of rotation of cutting edge 120). FIG. 25A illustrates a first, starting position. FIG. 25B illustrates a second position where shield 140 is retracted. FIG. 25C illustrates a gradual return to the first, starting position (FIG. 25D). The benefits of retraction are described above.

FIGS. 26A through 26D illustrate another embodiment wherein the retraction of outer tube 130 and/or morcellation is accomplished with a spring loaded or trigger actuated mechanism, both of which are configured to expand and retract. The spring mechanism may be initiated by a button. In this embodiment, outer tube 130 is configured for attachment to a spring 300. Pressing butting 215 compresses spring 300 against its bias and retracts shield 140 (FIG. 26B). This retraction permits large tissue mass 190 to be morcellated via the orange peeling or core methods. Pressing button 215 further into a second position (FIG. 26C) releases the spring 300 releasing the shield 140 also releasing distally into the original position. Additionally, when button 215 is pressed either in button 215's first or second position, an electric circuit 310 may form with inner tube 110 or cutting edge 120 to cause rotation for cutting. Hence, morcellation is accomplished both when shield 140 is retracted and when it returns to its original position.

The buttons may be progressively actuated. Thus a medical practitioner would press button 215 half-way to its first position to begin morcellation. However, as morcellation proceeded, the surgeon could press the button again further to a second position to release shield 140. This allows the surgeon to gain a view of mass 190 for morcellation without blocking the surgical view by shield 140 at first.

This embodiment helps reduce tissue injury. This is because shield 140 projects out creating a barrier with nearby organs and tissue at the end of morcellation. At the start of morcellation, however, it is retracted, allowing a surgeon to morcellate quickly and efficiently without interference of shield 140.

Figure 27A:
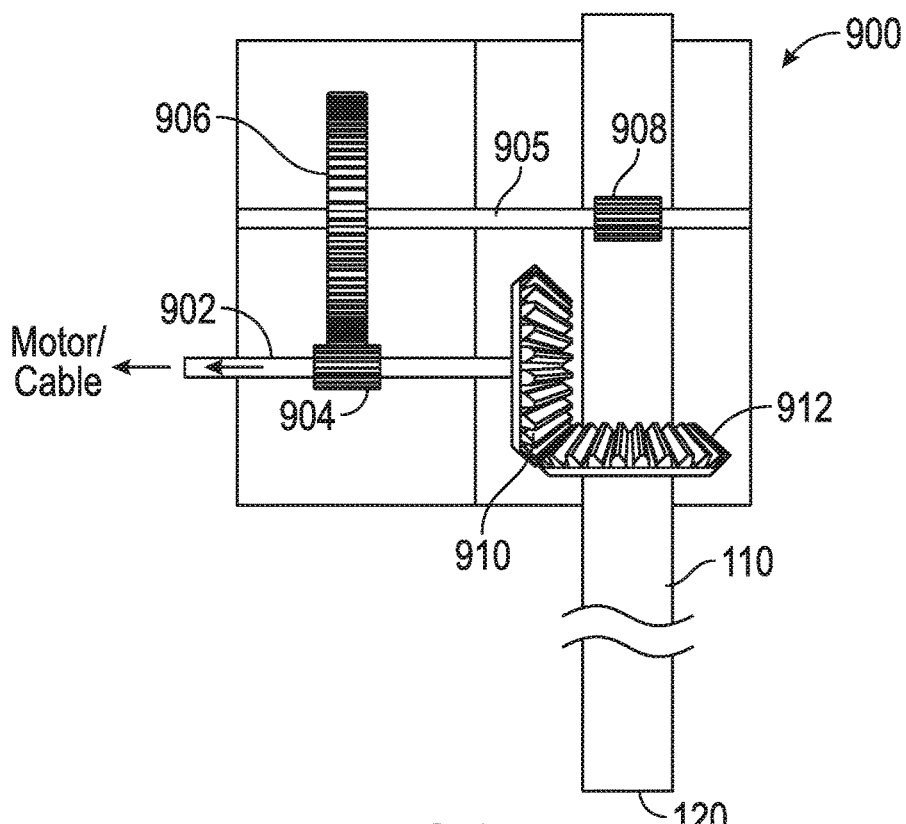
FIGS. 27A, 27B, 27C show an embodiment wherein the speed of the retraction or retrieval of the tissue with a tenaculum may be coupled to or a proportion of the speed of rotation of the cutting edge.
Figure 27B:
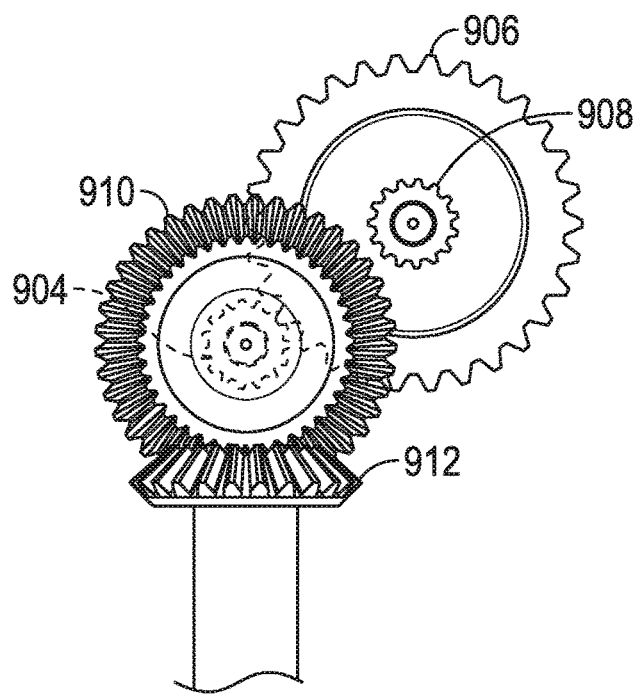
Figure 27C:
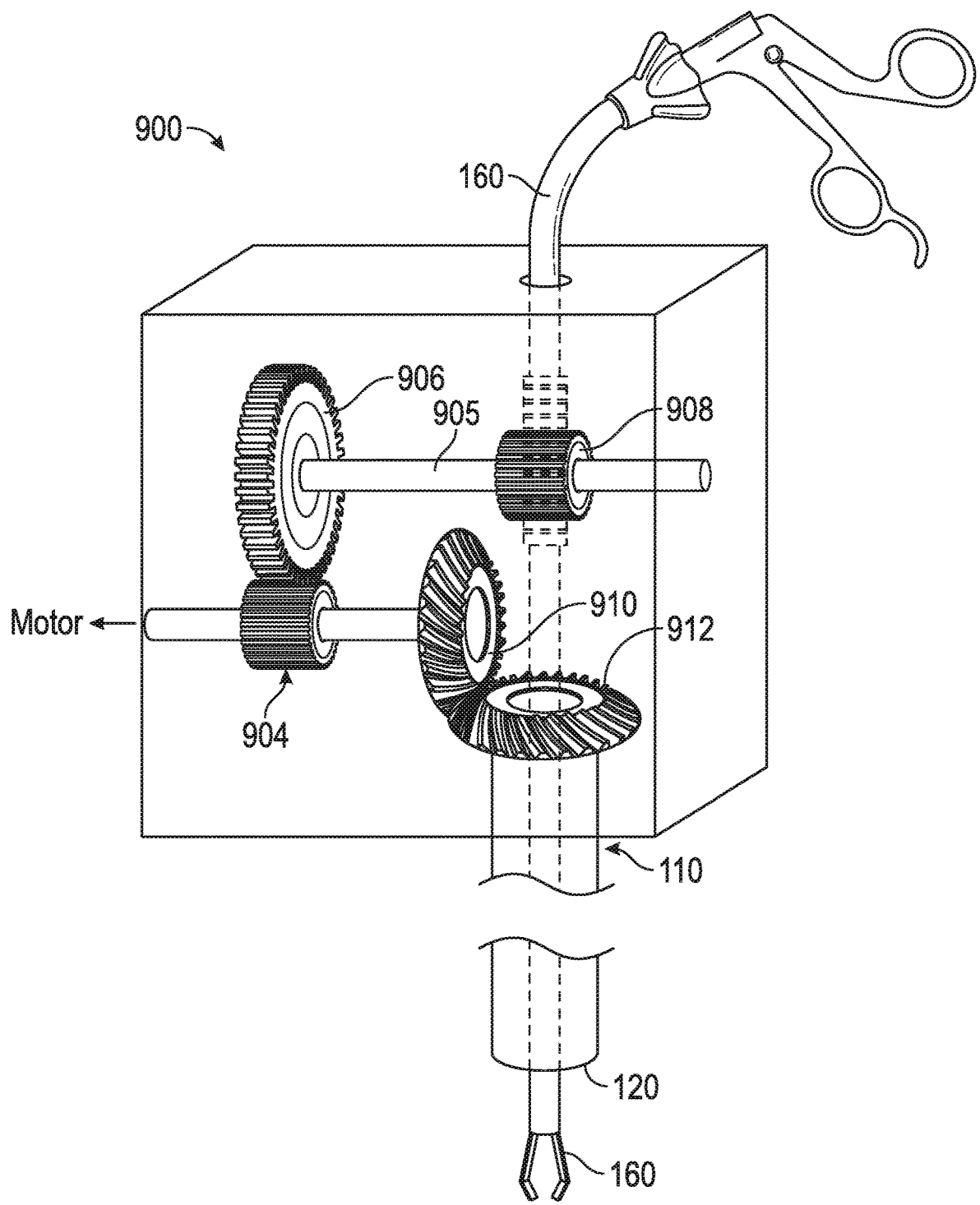

In yet another embodiment, as shown for example in FIGS. 27A-C, the speed of the retraction or retrieval of the tissue with tenaculum 160 may be coupled to or a proportion of the speed of rotation of the cutting edge 120. In other words, the pull rate that tenaculum 160 moves along the longitudinal axis may be based on, and change based on, the rotational speed of cutting edge 120. The faster the rotational speed of cutting edge 120, the faster tenaculum 160 may be pulled along the longitudinal axis, and the slower the rotational speed of cutting edge 120, the slower tenaculum 160 may be pulled along the longitudinal axis.

FIGS. 27A-C show a gear box 900 that includes a motor-driven shaft 902, a secondary drive shaft 905 having mounted thereto a first driver gear 904, a second, larger speed reduction gear 906 and a final driver gear or drum 908 (collectively a tenaculum gear drive). The gear box 900 also contains a first bevel gear 910 mounted to the motor-drive shaft 902 and driving a perpendicular second bevel gear 912 mounted to the shaft driving the cutting edge (collectively the cutting gear drive).

As seen in FIG. 27C, the final driver gear 908 urges the linear movement of the tenaculum and any tissue gripped thereby. For example, the tenaculum may be equipped with a gear rack that rides on the final driver gear 908. The larger diameter of the speed reduction gear 906 reduces the speed of the motor rotation and increase torque output for moving the tenaculum. At the same time, the bevel gears 910 and 912 maintain or increase the speed of the motor rotation when driving the cutting edge. Because the cutting edge and tenaculum are driven off of the same motor but at different ratios, their movement is proportionately tied. The tenaculum moves less, but in a particular proportion and same direction, as the cutting edge. Both may also reverse, retracting the tenaculum and reversing rotation of the cutting edge.

As driven by the gear box 900, the automated tenaculum may pull tissue into the inter lumen from the inner tube's distal end 111 towards it's proximal end 112. In embodiments, once tenaculum moves sufficiently proximal, drum 908 grasps the tissue and applies the pull force directly on the tissue. Additional drums may be used within the inner tube or device as necessary to secure the tissue grasping and pulling by drum 908.

It should be noted, however, that the pull rate of the tissue is a function of the tissue thickness as well as the RPM. For example, a high RPM on denser tissue will have a lower pull force, while a low RPM on a softer tissue will have high a strong pull effect. Density of the tissue matters with respect to pull rate.

As driven by the gear box 900, the automated tenaculum may pull tissue at a rate of one inch per 5 seconds and be coupled to a cutting edge rotational rate of 1200 rpm-2000 rpm. In another coupling ratio, the automated tenaculum may pull the tissue at a rate of one inch per 10 seconds for a cutting edge rotational rate of 700 rpm-2000 rpm. The tenaculum pull rates may also range from 3 to 15 seconds per inch for a cutting edge rotation range of 300 to 1200 rpm. A medical practitioner may be able to chose the desired rate by a morcellation speed control positioned on the gear box 900 or handle 200 (which may house all or a portion of the gear box 900 and/or its components).

In another coupling ratio, the automated tenaculum may pull the tissue at a rate of one-half inch per 15 to 20 seconds for a cutting edge rotational rate of 125 rpm to 850 rpm. In another coupling ratio, the tenaculum may pull the tissue at a rate of one inch per 15 to 20 seconds for a cutting edge rotational rate of 350 rpm to 1450 rpm. In another coupling ratio, the tenaculum may pull the tissue at a rate of 1.5 inches to 2 inches per 15-20 seconds for a cutting edge rotational rate of 700 rpm to 2000 rpm.

Selection of the gears within the gear box 900 allows the ratios of the tenaculum movement to be established relative to the movement of the cutting edge. The rotation of the final driver gear 908 can be ¼ to ⅒ (or an even lower fraction such as ¹⁄₁₀₀ of) the speed of the second bevel gear 912.

Gear box 900 may be located within handle 200. Inner tube 110 and outer tube 130 may transverse handle 200, or be integral to handle 200, or be part of handle 200. Handle 200 may also include a motor to power the gears and mechanics within gear box 900.

The inventor at times has noticed that less experienced surgeons will try to draw tissue into the cutting edge too quickly and/or have the speed of the cutting edge moving too slowly. In addition, less experienced surgeons attempt excessively combine push and pull forces described earlier (pushing the morcellator into the patient and at the same time pulling tissue). Advantageously, coupling the speed of the tenaculum to the speed of the cutting edge avoids mistakes by limiting, controlling or automating the draw rate of tenaculum, in particular so that the draw rate of the tissue is coupled to the capacity of the cutting edge to morcellate the tissue (i.e. morcellation or cutting rate).

Although the figures show a mechanical implementation of coordinating or coupling the speed of the tenaculum to the speed of the cutting edge, such coupling could be accomplished by a range of mechanical and/or electro-mechanical means. For example, alternative gear systems could modulate the ratios of the tenaculum movement relative to the movement of the cutting edge. In other embodiments, two separate motors could be employed for example, one for each of the tenaculum and cutting edge, and these motors could have speeds coordinated by a circuit or software controls.

Additional functional features could be effected with electronic coupling of the movements. For instance, torque in either of the gear systems could be monitored to prevent overloading—a torque spike could cause motor shutoff for example. The ratio of the cutting edge and draw rate of the tenaculum could be lower during initial tissue capture and slow down as the tissue reaches the cutting edge. The absence of tissue and a jump in speed (or drop in current of the motor) could be used to implement a slowdown of both motors (or a complete shutoff for safety reasons).

Although a range of notch configurations are possible embodiments of the present invention, the inventors have determined that convergent and non-convergent notches work particularly well in certain surgical environments to capture tissue fragments.

Convergent notches, as described herein, refer to notches that have at least one pair of edges that generally converge as they extend from the lateral edge toward a center line of the shield. Convergent notches could converge by having one, or both, edges angled toward each other so as to better capture and direct tissue captured from the rotation of the cutter.

Figure 28A:
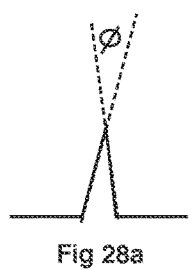
FIGS. 28a, 28b, 28c, 28d, 28e, 28f, 28g, 28h, 28i, 28j, 28k, 28l, 28m, 28n, 28o, 28p, 28q show embodiments of convergent and non-convergent notches configured to capture loose tissue fragments on a shield of a morcellator.
Figure 28B:
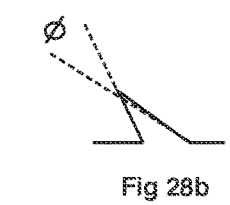
Figure 28C:
Figure 28D:
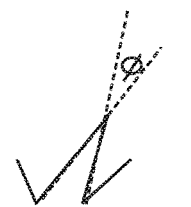
Figure 28E:
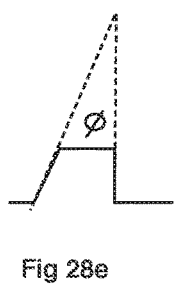
Figure 28F:
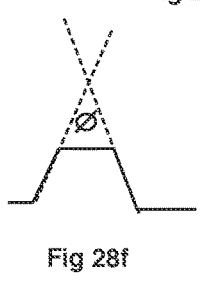
Figures 28G, 28H:
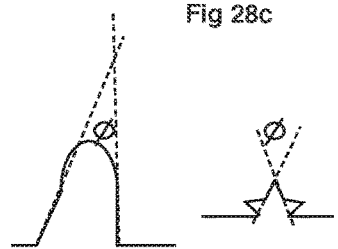
Figure 28I:
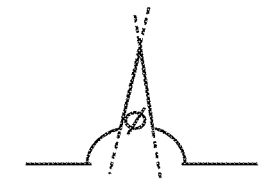

FIG. 28 through FIG. 28d show embodiments of converging notches wherein a pair of edges converge to form an angle less than 90 degrees. Preferably, the angle of convergence is between 20 to 70 degrees, though in some embodiments that angle of convergence may be greater than 90 degrees, but preferably not greater than 130 degrees. The inventor has found that angles greater than 130 degrees limit the ability of the notches to catch and trap tissue as the notches lack a sufficient crevices to hold the tissue, unless the notch as sub-notches which have the preferred angle of convergance.

Edges in converging notches need not necessarily converge, but were one to continue extending the edges they would converge eventually. FIG. 28e through FIG. 28i show embodiments of notches wherein the edges do not converge but an angle of intersection of extended edges show an angle of convergence that is less than 90 degrees.

Figure 28Q:
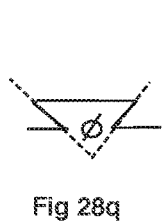
Figure 28J:
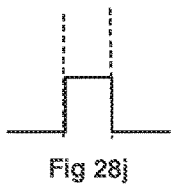
Figure 28K:
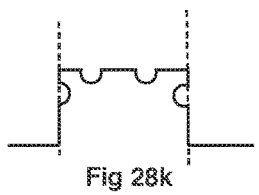
Figure 28L:
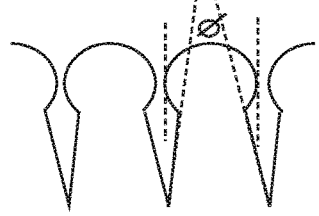

Additionally, a pair of edges measured for convergence may form only a portion of a notch. As a result, notches need not be entirely V-shapes, but may have portions that are circular shaped or other polygonal shapes. Mixed shapes as shown in FIG. 3 and FIG. 28L have a pair of edges which form of a portion of a notch and converge within the desired angle range.

It should also noted that the edges need not be perfectly straight; tangent lines may be drawn on curve to determine the measuring edge and they only need to generally converge enough to direct the tissue within the desired angle range. Additionally, for squiggly, curvy or nonlinear edges, a linear regression of points may be taken to determine the average edge and measure convergence.

Examples of convergent notches are also shown in FIGS. 2, 3 and 24. Each of these notches starts at the free lateral edge of the shield with a v-like shape, wherein the converging edges defining the notch are straight. FIG. 24 shows a particular orientation of the convergent notches, wherein the notches are directed more distally along the axis of the morcellator shaft. The more distal orientation (as defined by a line bisecting the angle between the two edges of the convergent notch edges) is in a range of about 20 to 80 degrees relative to the longitudinal axis of the morcellator shaft. This more closely aligns mouth of the notches with the curving surface of the shield in FIG. 24 and may therefore enhance tissue capture.

Non-convergent notches may also be employed on a shield 140 to capture tissue. Non-convergent notches, as described herein, refer to notches that have at least one pair of edges that are parallel. These include square or rectangular notches. FIGS. 28j and 28k show embodiments of non-convergent notches.

It should be noted that circular shaped notches are both convergent and non-convergent. Tangent lines between two edges may be drawn to determine the angle of convergence. However, two possible tangent lines, are parallel and therefore non-convergent, while other extended tangent lines show convergence. FIGS. 28n-28p illustrate convergent and non-convergent circle shaped notches wherein the shown angle of convergence is less than 90 degrees.

Figure 28M:
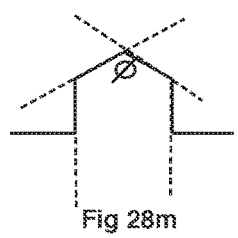
Figure 28N:
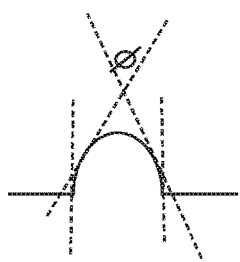
Figure 28O:
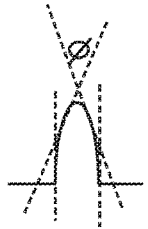
Figure 28P:
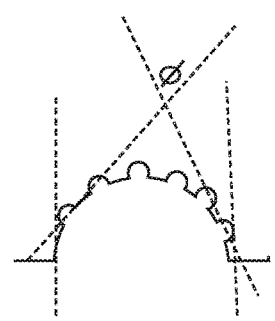

FIGS. 28l and 28m show embodiments where the notch may be both convergent and non-convergent, having a pair of parallel edges and a pair convergent edges. FIG. 28m shows a convergent notch with an obtuse angle of convergence greater than 90 degrees but less than 180 degrees.

Divergent notches may also catch tissue, but not as efficaciously. As described herein, divergent notches refer to notches that have at least one pair of edges that generally converge as they extend from the center line of the shield towards a lateral edge, as shown in FIG. 28q. For divergent edges, the angel of preferred convergence is between 20 to 70 degrees, though in some embodiments that angle of convergence may be greater than 90 degrees, but preferably not greater than 130 degrees. Nonetheless, it is possible to combine with divergent and convergent edges to create an efficacious tissue capture.

It should be noted that since arms may be inverse notches (for example, one or more notches creates an arm in between), similarly convergent, non-convergent and divergent arms work particularly well in certain surgical environments to capture tissue fragments.

Convergent arms, as described herein, refer to arms that have at least one pair of edges that generally converge as they extend from the center line of the shield to the lateral edge. Non-convergent arms, as described herein, refer to arms that have at least one pair of edges that are parallel. Divergent arms, as described herein, refer to arms that have at least one pair of edges that generally converge as they extend from the lateral edge to the center line of the shield. Because adjacent arms create notches and vice-versa, all of the variations for arms described herein also apply as variations for the notches.

Through experimentation, the inventors have determined dimensions and proportions suitable for a shield 140 and distal portion of a morcellator. A preferred distance L5 between outer tube's distal end 131 and inner tuber's distal end 111, wherein the inner tube's distal end has a cutting edge 120, is between 1 mm to 4 mm, but the invention may function without an offset, a minor offset of a (fraction of a millimeter), or a more substantial offset of 10 mm or more. Experimentation has shown that in circumstances of morcellating tissue in the peritoneal cavity or abdomen where there are nearby vital structures at risk of morcellation and surgeons have poor visibility, a 2 mm offset works particularly well. In these circumstances, identifying the cutting edge as closely as possible to the distal end of the outer tube enhances safety.

The diameter of inner tube 110 may range from 3 mm (for circumstances of micro-surgical morcellation) up to 15 mm (for circumstances large morcellation). Similarly, the diameter of outer tube 130 may range from 4 mm to 18 mm, depending on the circumstance. Depending on the embodiment, the difference in diameter between the inner tube and outer tube is preferably between 1 mm to 5 mm. Experimentation has shown that diameter differences greater than 10 mm are not functionally practical when operating in a minimally invasive context. The relative proportions in diameter between the inner and outer tubes is preferably between 50% to 95%, though it is more preferable between 60% to 90%. Experimentation has shown that an embodiment with an inner tube 110 having a 10 mm diameter and outer tube 130 having a 12 mm diameter works particularly well when morcellating tissue in the abdominal or peritoneal cavity.

Shield length L3 is preferably 15 mm but could range from 10 mm to 20 mm in full length to achieve maximum tissue capture with ease of use in the abdominal cavity. Shield length L3 may also be between 2 mm to 30 mm, but experimentation has shown that lengths L3 greater than 30 mm is not functionally practical when operating in a minimally invasive context.

Shield 140 is shown to be most effective when its diameter (or its effective diameter if the shield does not have sufficient circumference) is equal or greater to the diameter of the outer tube. Experimentation has shown that when shield diameters are 10 mm or more greater than the outer tube's diameter, the shield is not as functionally practical when operating in a minimally invasive context. Therefore, it is preferred that the outer tube's diameter is not less than 50% of the shield's diameter.

Experiments have shown inventors that notches 141 and/or arms 142 on shield 140 function well being between 1 mm to 7 mm wide. Their preferred angle of convergence is 20 to 70 degrees, but preferably not greater than 130 degrees. Their depth may be 10% to 90% of the width or widest portion of shield 140.

In an embodiment, the outer tube is 12 mm in diameter, the inner tube is 10 mm in diameter, and their offset distance L5 is 2 mm. In this embodiment, shield has a 12 mm diameter and may be 10 mm to 20 mm long. The shield has a plurality of notches that are 2 mm to 7 mm wide and 2 mm to 8 mm deep.

A morcellator may be made of steel, plastic, polymers, ABS, rubber, polyurethane, any medical grade or biocompatible material, or any combination thereof.

Additionally, there is a method 1400 for trapping morcellated tissue. The operations of method 1400 presented below are intended to be illustrative. In some embodiments, method 1400 may be accomplished with one or more additional operations not described, and/or without one or more of the operations discussed. Additionally, the order in which the operations of method 1400 are described below is not intended to be limiting. Alternative methods are described throughout this specification, particularly in descriptions about FIGS. 3, 22, 26, and 27.

According the method 1400, a surgeon may grasp a tenaculum and insert it into the inner lumen of a morcellator, configured as an inner lumen with a distal cutting edge surrounded by an outer tube. The tenaculum may pull the grasped tissue into the inner lumen and bring the tissue mass in contact with the cutting edge.

Cutting member may be rotated, and while the tissue is being pulled into the inner lumen, the rotation of the cutting member may sever portion of the grasped tissue.

Fragments of the severed tissue may begin to rotate along with the rotating cutting member.

Fragments of tissue may be caught within notches and arms on a sidewall of a denticulate shield, wherein shield 140 projects distally from the morcellator's outer tube.

Additionally, the pull force of morcellation may be modulated or related in proportion to the rotational rate of the cutting edge.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation. Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

The invention claimed is:
1. A surgical device comprising:
an inner tube having a first open end and a second open end, the inner tube having a first diameter;
an outer tube having a second diameter, the second diameter being greater than the first diameter, at least a portion of the outer tube being configured to encompass the inner tube;
a cutting edge positioned proximate to the first open end of the inner tube; the cutting edge being configured to rotate;
a denticulate shield configured to project distally from a first end of the outer tube and extend around a portion of a circumference of the outer tube, the denticulate shield including at least one notch, wherein the at least one notch is positioned on a first sidewall of the denticulate shield, wherein the outer tube and the denticulate shield are configured to move along a longitudinal axis while the inner tube remains stationary.

2. The surgical device of claim 1, wherein a top surface of the denticulate shield is planar to a top surface of the outer tube.

3. The surgical device of claim 1, wherein the at least one notch is configured to catch loose fragments of tissue.

4. The surgical device of claim 1, wherein the denticulate shield includes a plurality of arms, the plurality of arms being positioned on both sides of the at least one notch, the plurality of arms extending around a portion of a circumference of the inner tube.

5. The surgical device of claim 4, wherein the plurality of arms extend past a circumference of the outer tube.

6. The surgical device of claim 1, further comprising:
a plurality of notches, the plurality of notches being positioned on the first sidewall of the denticulate shield, and on a second sidewall of the denticulate shield.

7. The surgical device of claim 1, wherein a distal end of the denticulate shield is rounded.

8. The surgical device of claim 1, wherein the denticulate shield and the outer tube form a unitary piece.

9. A surgical device comprising:
an inner tube having a first open end and a second open end, the inner tube having a first diameter;
an outer tube having a second diameter, the second diameter being greater than the first diameter, at least a portion of the outer tube being configured to encompass the inner tube;
a cutting edge positioned proximate to the first open end of the inner tube; the cutting edge being configured to rotate;
a denticulate shield configured to project distally from a first end of the outer tube and extend around a portion of a circumference of the outer tube, the denticulate shield including at least one notch, wherein the at least one notch is positioned on a first sidewall of the denticulate shield
wherein a distal end of the denticulate shield is configured to move between all or a portion of a distance between a first position and a second position; wherein the first position the distal end of the denticulate shield is distal to the first open end of the inner tube; wherein in a second position the distal end of the denticulate shield is configured to be positioned proximal to the first open end of the inner tube; wherein the outer tube is configured to move along a longitudinal axis, the denticulate shield being configured to dependently move with the outer tube.

* * * * *